US009879056B2

(12) United States Patent
Tu et al.

(10) Patent No.: US 9,879,056 B2
(45) Date of Patent: Jan. 30, 2018

(54) INSECTICIDAL PROTEIN

(71) Applicants: ZHEJIANG UNIVERSITY, Hangzhou, Zheijiang Province (CN); CHINA NATIONAL RICE RESEARCH INSTITUTE, Hangzhou, Zhejiang Province (CN)

(72) Inventors: Jumin Tu, Hangzhou (CN); Ju Luo, Hangzhou (CN); Hao Chen, Hangzhou (CN); Xiaobo Zhang, Hangzhou (CN)

(73) Assignees: China National Rice Research Institute, Hangzhou, Zhejiang (CN); Zhejiang University, Hangzhou, Zhejiang (CN)

( * ) Notice: Subject to any disclaimer, the term of this patent is extended or adjusted under 35 U.S.C. 154(b) by 0 days.

(21) Appl. No.: 15/039,234

(22) PCT Filed: Nov. 18, 2014

(86) PCT No.: PCT/CN2014/001029
§ 371 (c)(1),
(2) Date: Dec. 30, 2016

(87) PCT Pub. No.: WO2015/074325
PCT Pub. Date: May 28, 2015

(65) Prior Publication Data

US 2017/0121731 A1 May 4, 2017

(30) Foreign Application Priority Data
Nov. 25, 2013 (CN) .......................... 2013 1 0600148

(51) Int. Cl.
| | |
|---|---|
| *C12N 15/32* | (2006.01) |
| *C07K 14/325* | (2006.01) |
| *A01H 5/00* | (2006.01) |
| *C12N 15/82* | (2006.01) |
| *C07K 14/32* | (2006.01) |
| *A01N 37/46* | (2006.01) |

(52) U.S. Cl.
CPC ............ *C07K 14/325* (2013.01); *A01N 37/46* (2013.01); *C07K 14/32* (2013.01); *C12N 15/8286* (2013.01)

(58) Field of Classification Search
CPC .................................................. C12N 15/8286
See application file for complete search history.

(56) References Cited

U.S. PATENT DOCUMENTS 5,770,696 A 6/1998 Warren et al.
6,752,992 B2 * 6/2004 Schnepf ............... C07K 14/325 424/185.1

FOREIGN PATENT DOCUMENTS

| | | |
|---|---|---|
| CN | 101507472 | 8/2009 |
| WO | 98/44137 | 10/1998 |
| WO | 02/078437 | 10/2002 |
| WO | 03/075655 | 9/2003 |

OTHER PUBLICATIONS

GenBank: ABB72459.1 (2007).*
GenBank: AIT93182.1 (2014).*
Hernández-Martínez et al (Journal of Invertebrate Pathology 113 (2013) 78-81).*
Wu et al (Theor Appl Genet (2002) 104:727-734).*
Liu et al (Letters in Applied Microbiology 45 (2007) 432-438).*
Bel et al(Toxins 2017, vol. 9, p. 131).*
Chakroun et al (Microbiol. Mol. Biol. Rev. Jun. 2016 vol. 80 No. 2 pp. 329-350).*
Guo et al (PNAS 2004 (101)25, 9205-9210).*
Liu et al (Lett Appl Microbiology. Oct. 2007;45(4):432-438).*
Tang, Wei, Yang, Zhou. "Development of Transgenic Insect-resistant Indica Rice with a cry1Ab Gene." Journal of Huazhong Agricultural University, 2007, 26 (2): 157-160.
Schnepf et al, "Bacillus thuringiensis and its pesticidal crystal proteins." Microbiol Mol Biol Rev 1997, 62: 775-806.
Li, Changyou, Li, Guoxun, Zhang, Jie, Song, Fuping & Huang, Dafang. "Biological characteristics of Bacillus thuringiensis strain B-Hm-16 and identification of its cry-type genes." Journal of Qingdao Agricultural University (Natural Science), 2007, 24 (1): 1-4.
Liu, Rongmei, Zhang, Jie, Gao, Jiguo et al. "The Research on vip3A Genes from Bacillus thuriniensis Strains." High Technology Letters. 2004, 14(9):39-42.
Ni, Wanchao, Guo, Sandui. "Development of Transgenic Insect-resistant Cotton Plants." Scientia Agricultura Sinica. 1998, 31(2):8-13.
Zhu, Zhen, Deng, Zhaoyang, Wu, Qian & Xu, Honglin. "Development of highly efficient insect-resistant transgenic rice." Journal of Yunnan University (Natural Science). 1999, 21.
Barth H, Blocker D, Aktories K. "The uptake machinery of clostridial actin ADP-ribosylating toxins-a cell delivery system for fusion proteins and polypeptide drugs." Naunyn Schmiedebergs Arch Pharmacol. 2002, 366(6):501-512.
Barth H, Aktories K, Popoff MR, et al. "Binary bacterial toxins: biochemistry, biology, and applications of common Clostridium and Bacillus proteins." Microbiol Mol Biol Rev. 2004,68(3):373-402.

(Continued)

*Primary Examiner* — Lee A Visone
(74) *Attorney, Agent, or Firm* — Michael Best & Friedrich LLP

(57) ABSTRACT

Provided are an artificially designed and modified insecticidal protein or a segment thereof. The insecticidal protein belongs to a Vip3A-type insecticidal protein. The protein or the segment thereof has an insecticidal activity against a pest, especially a lepidoptera pest. Also provided are a nucleic acid for coding the protein or the segment thereof, an insecticidal composition, a DNA constructor, and a transformed microorganism or a plant comprising the nucleic acid, and a method for controlling a pest, especially a plant pest.

47 Claims, 2 Drawing Sheets

(56) References Cited

OTHER PUBLICATIONS

Crickmore N. The Vip nomenclature. http://www.lifesci.sussex.ac.uk/home/Neil_Crickmore/Bt. 2008.

Estruch JJ, Warren GW, Mullins MA, et al. "Vip3A, a novel Bacillus thuringiensis vegetative insecticidal protein with a wide spectrum of activities against lepidopteran insects." Proc Natl Acad Sci USA. 1996,93(11):5389-5394.

Shen, Jianru, Hou, Minyu, Guo, Wei, "Identification and Cloning of vip3A Genes from isolates of Bacillus thuringiensis and their bioactivity analysis," Acta Microbiologica Sinica, 2009, 49(1):110-116.

Estela A, Escriche B, Ferre J. "Interaction of Bacillus thuringiensis toxins with larval midgut binding sites of Helicoverpa armigera (Lepidoptera:Noctuidae)." Appl Environ Microbiol. 2004,70(3):1378-1384.

Fang J, Xu X, Wang P, Zhao J Z, Shelton AM, Cheng J, Feng MG, Shen Z. "Characterization of Chimeric Bacillus thuringiensis Vip3 Toxins." Appl Environ Microbiol.2007,73(3): 956-961.

Fraley RT, Rogers SG, Horsch RB, et al. "Expression of bacterial genes in plant cells." Proc. Natl. Acad. Sci. USA. 1983,80:4803-4807.

Griffitts JS, Aroian RV. "Many roads to resistance: how invertebrates adapt to Bt toxins." Bioessays. 2005,27(6):614-624.

Gould F. "Broad-spectrum resistance to Bacillus thuringiensis toxins in Heliothis virescens." Agriculture Sciences.1992,89:7986-7990.

Han S, Craig JA, Putnam CD, Carozzi NB & Tainer JA. "Evolution and mechanism from structures of an ADP-ribosylating toxin and NAD complex." Nature Structural & Molecular Biology. 1999, 6:932-936.

Herdt RW. "Research priorities for rice biotechnology." Rice biotechnology. 1991, 6,19-54.

High SM, Cohen MB, Shu QY, et al. "Achieving successful deployment of Bt rice." Trends Plant Sci.2004,9(6):286-292.

Khush, GS. "What it will take to feed 5.0 billion rice consumers in 2030." Plant Molecular Biology. 2005,59:1-6.

Lee MK. "Resistance to Bacillus thuringiensis Cry1A δ-endotoxins in a laboratory-selected Heliothis virescens strarin is related to receptor alteration." American Society for Microbiology. 1995,61:3836-3842.

Liu J et. al., GenBank Accession No. ABB72459.1 GenBank Database (Sep. 30, 2007).

Liu QQ, Yao QH, Wang HM, Gu MH. "Endosperm-specific Expression of the Ferritin Gene in Transgenic Rice (*Oryza sativa* L.) Results in Increased Iron Content of Miling Rice." Journal of genetics and genomics. 2007,31(5):518-524.

McGaughey WH. "Insect Resistance to the Biological Insecticide Bacillus thuringiensis." Science. 1985,229(4709):193-195.

Perlak, FJ. t al. "Insect-resistance cotton plants." Bio/Technology. 1990,8:939-943.

Rang C, Gil P, Neisner N, Rice JV, Frutos R."Novel Vip3-related protein from Bacillus thuringiensis." Applied and Environmental Microbiology.2005,71(10):6276-6281.

Yang R, Tang Q, Wang H, Zhang X, Pan G, Wang H, Tu J. "Analyses of two rice (*Oryza sativa* L.) cyclin-dependent kinase inhibitors and effects of transgenic expression of OsiICK6 on plant growth and development." Annals of Botany.2011,107:1087-1101.

Tabashnik BE, Liu YB, Finson N, Masson L & Heckel DG. "One gene in diamondback moth confers resistance to four Bacillus thuringiensis toxins." Proceedings of the National Academy of Sciences.1997,94:1640-1644.

Tu J, Datta K, Alam MF, Khush GS, Datta SK. "Expression and function of a hybrid Bt toxin gene in transgenic rice conferring resistance to pest." Plant Biotech.1998,15(4):195-203.

Tu J, Zhang G, Datta K, Xu C, He Y, Zhang Q, Khush GS, and Datta SK. "Field performance of transgenic elite commercial hybrid rice expressing Bacillus thuringiensis δ-endotoxin." Nature/Biotech. 2000,18:1101-1104.

Van Rie. "Mechanism of insect resistance to the microbial insecticide Bacillus thuringiensis." Science. 1990, 247:72-74.

Whalon ME, Wingerd BA. "Bt mode of action and use." Arch Insect Biochem Physiol. 2003,54:200-211.

Lee MK, Walters FS, Hart H, et al. "The mode of action of the Bacillus thuringiensis vegetative insecticidal protein Vip3A differs from that of Cry1Ab delta-endotoxin." Appl Environ Microbiol. 2003, 69(8):4648-4657.

Yu CG, Mullins MA, Warren GW, et al. "The Bacillus thuringiensis vegetative insecticidal protein Vip3A lyses midgut epithelium cells of susceptible insects." Appl Environ Microbiol.1997, 63(2):532-536.

\* cited by examiner

INSECTICIDAL PROTEIN

FIELD OF THE INVENTION

The present invention relates to the fields of plant genetic engineering and molecular breeding technology. In particular, this invention relates to artificially designed and modified insecticidal protein polypeptides or fragments thereof, which have insecticidal activities against insect pests. The present invention also provides nucleic acids encoding the insecticidal protein polypeptides or fragments thereof, insecticidal compositions, DNA constructs, as well as transformed microorganisms and plants comprising the nucleic acids. These compositions are useful in the methods for controlling pests, particularly plant pests. This invention also relates to the use of the nucleic acids or DNA constructs in improving plant stress resistance.

BACKGROUND

Rice is one of the most important cereal crops in the world, which is also an important cash crop in China. Nearly 50% of the world's population feed on rice [Khush, 2005]. Rice is mainly distributed in Asia, and has been planted in Europe, America, Africa and Oceania as well. However, rice is also one of the cereal crops that suffer the most from pests. Based on non-exhaustive statistics, the annual loss of rice caused by rice pests such as those from Lepidoptera, etc. has been over 10 million tons globally [Herdt, 1991; Zhu Zhen et al., 1999]. The use of pesticide serves well on pest control, but it also causes severe contamination of toxic residues to human. The pesticide residues in environment may contaminate air and water resources, destruct soil properties; and while killing pests, many beneficial insects are killed as well, which has severely disrupted the ecological balance; moreover, prolonged use of pesticide may also induce resistance in pests; it is therefore believed to be a more environment friendly and more effective control method by means of selectively breeding insect-resistant rice varieties, and enhancing resistance in rice itself. However, due to the lack of insect-resistant resources from rice varieties themselves, and the period of selective breeding of new variety using traditional breeding approach is fairly long, the selective breeding of new insect-resistant rice variety has always been a problem. Recently, with the fast development in cell biology and molecular biology, scientists have successfully integrated exogenous insect-resistant genes into rice genome by transformation using bio-genetic engineering technique, enabling the production of insect-resistant proteins in rice itself that can also be inherited stably in order to control pests [Tu et al., 1998 and 2000; Wei Tang and Zhou Yang et al., 2007]. Such technique can break the species barrier and achieve the direct selection and effective pyramiding of genes, which has substantially improved the breeding efficiency.

*Bacillus thuringiensisis* is currently the most extensively applied and studied insecticidal microorganism in the world. During the sporulation of *Bacillus thuringiensis*, it can form and secret some parasporal crystals consisting of insecticidal crystal proteins (ICPs or Cry), which have killing activities specific for arthropods such as insects from Lepidoptera (cryI), Lepidoptera and Diptera (cryII), Coleoptera (cryIII) and Diptera (cryIV), etc., as well as animal and plant nematodes (Schnepf et al., 1998; Changyou Li et al., 2007). However, long term growing a unitary Bt gene transgenic crop may also cause resistance in pests. In recent decades, it has been found that different pests show resistance to ICPs and ICPs-transgenic plants at different levels [McGaugher et al., 1985; Van, 1990; Gould, 1992; Lee, 1995; Tabashnik et al., 1997; Wanchao Ni and Sandui Guo, 1998; High et al., 2004; Griffitts J S and Aroian R V, 2005].

More recently, it is found that Bt can secret a new type of insecticidal protein, i.e. *Bacillus thuringiensis* Vegetative Insecticidal Protein (abbr. VIP) during vegetative growth, which does not form crystal, has no homology with ICPs in the evolution of amino acid sequences, has different insecticidal mechanism from ICPs as well and does not present any similarity in structure either [Estruch et al, 1996; Yu et al, 1997; Estruch et al, 1998; Lee et al, 2003; Estela et al, 2004; Rang et al, 2005]. It exhibits certain insecticidal activity against various agricultural pests from Lepidoptera, Coleoptera etc. [Estruch et al, 1996; Warren et al, 1998], and the insecticidal activity is at nanogram level against certain pests [Rongmei Liu et al., 2004]; additionally, it is also toxic to pests that are insensitive to ICPs such as *Agrotis ipsilon* [Estruch et al, 1996; Yu et al, 1997]. This provides a new option for controlling agricultural pests that are insensitive or resistant to ICPs.

VIP is a type of extracellular toxic protein that is secreted by *Bacillus thuringiensis* in its mid-log phase of vegetative growth [Schnepf et al, 1998], and widely exists in Bt in nature. By 2008, 37 species in 8 classes have been identified and isolated [Crickmore, 2008]. Previous studies have shown that these VIPs are relatively conservative genetically. In general conditions, at least 75% of them are present in the supernatant, and compared to ICPs, they are thermally unstable and can be deactivated by treating at 95° C. for 20 min [Estruch et al, 1996].

In the system of nomenclature, according to the homology of their protein sequences, VIPs can be categorized into the following three classes: i.e. VIP1, VIP2 and VIP3 [Crickmore et al, 2008]. VIP1 and VIP2 together construct a binary toxin of insecticidal specificity for insects from Galerucinae in Coleoptera [Warren et al, 1998]; while VIP3 has insecticidal activity against numerous pests from families, genus and species in Lepidoptera on a relatively broad spectrum, with a deep study on its insecticidal mechanism as well [Estruch et al, 1998]. Till 2008, fifty-seven Vip genes have been identified and isolated [Crickmore, 2008].

As a binary toxin, VIP1 and VIP2 function separately in insecticidal mechanism [Barth et al, 2002 and 2004]. Vip2 gene is located at the upstream of Vip1 gene, their products can play their own roles independently [Barth et al, 2004], but only when these two proteins both exist and act synergistically, the maximal insecticidal toxicity of the toxin protein can be achieved [Warren et al, 1998]. Studies have shown that VIP1 can specifically bind to the receptor on mid-gut epithelial cell of insect larvae, and form a channel on cell membrane, providing a route for VIP2 to enter the cytoplasm of the target insect cell [Barth et al, 2004]. VIP2 containing NAD binding sites has ADP-ribosyltransferase activity, which can transfer ribosyl to actin along with the release of nicotinamide, resulting in the blocked polymerization of actin monomers that affect the construction of cytoskeleton, thereby leading to the death of insect cells (Han et al, 1999).

The insecticidal mechanism of VIP3 exhibits primarily on the disruption of the insect mid-gut cells by the toxin [Whalon & Wingerd, 2003]. After being taken up by lepidopteran insects, VIP3A, which is 88 ku in full length, is hydrolyzed and activated by mid-gut trypsin therein. Activated VIP3A protein can bind to unknown receptor molecules (80 ku and 100 ku) on BBMVs of the sensitive larval mid-gut, and form an ion-channel type pore on the mid-gut epithelial cell, which induces apoptosis of insect cell and caryolysis, eventually resulting in the death of insect [Lee et al, 2003]. Moreover, VIP3A protein is soluble once the pH is below 7.5 with its C' end not being cleaved as well, and these two receptors are also different from any known Cry receptor [Lee et al, 2003]; furthermore, VIP3A may also form a channel on artificial bilayer lipid membranes (BLMs) in the absence of any receptor [Warren et al, 1998; Lee et al, 2003].

Cytopathological experiments have shown that after feeding VIP3A(a) proteins to sensitive insects such as *Agrotis ipsilon* and *Spodoptera frugiperda* etc. for 72 h, the mid-gut epithelial goblet cells and columnar cells fall off completely from the basement membrane, resulting in the death of insects [Yu, et al, 1997]. The symptoms caused by Vip3A are similar to those caused by ICPs except a delay in time (Estruch et al, 1996). It thus can be seen that VIP3A has receptors and mode of action that are clearly distinct from ICPs, and the research and utilization of VIP3A are therefore important for expanding insecticidal spectrum, increasing insecticidal toxicity and preventing insects from developing resistance.

The molecular weight of ICP protein is generally 130~160 ku, and it is only soluble in high alkaline solution of pH>10. It is present in the form of protoxin without toxicity by itself, and after ingestion by insect larvae, it can be dissolved and cut into active polypeptides of 65~75 ku in the alkaline and reducing environment of mid-gut thereof; in contrast, VIP3A may be cut into active polypeptides of 62 ku by trypsin under weak alkaline conditions, even with pH slightly below 7.5 (Lee et al, 2003). In addition, ICP protein is a crystal protein secreted intracellularly, and VIP protein is an extracellularly secreted protein; during secretion, the N' end signal peptide of VIP1A protein (100 ku in full length) is cleaved prior to the formation of 80-ku mature toxin, while the N' end signal peptide of VIP3A protein (88 ku in full length) is usually not cleaved during secretion due to the absence of enzymatic cleavage site [Schnepf et al, 1998]. VIP protein has a broader insecticidal spectrum than Cry protein, and it also shows insecticidal activity against agricultural pests that are insensitive to ICP protein, such as *Agrotis ipsilon* etc. [Estruch et al, 1996].

Currently, the Vip3 gene that is highly resistant to rice borer has not yet been found and isolated from the natural strain of *Bacillus thuringiensis*. Accordingly, it is profound to artificially synthesize, modify and create the resource of Vip3 gene that is resistant to rice borer for addressing the insect-resistance duration issue faced by the use of Cry gene [McGaughey, 1985; Van, 1990; Gould, 1992; Lee, 1995; Tabashnik et al, 1997; Wanchao Ni and Sandui Guo, 1998; High et al, 2004].

SUMMARY OF THE INVENTION

To resolve the aforementioned problems, the inventors of the present application have developed a Vip3A gene named Vip3A rLr1, which is highly resistant to insect pests, in particular to lepidopteran pests, and especially demonstrates high resistance to rice lepidopteran pests such as *Chilo suppressalis, Tryporyza incertulas* and *Cnaphalocrocis medinalis* Guenee, etc., which has not been achieved by all other Vip3 genes heretofore identified and isolated; provide a plasmid vector system for transforming Vip3A rLr1 by *Agrobacterium*-mediated method and its construction, thereby providing a breeding method for transforming insect susceptible plants into insect-resistant plants, and transforming common main cultivated lines/varieties into main cultivated lines/varieties that are insect resistant. In particular, the present invention is directed to the following aspects:

1. A nucleic acid molecule selected from the group consisting of:
  a) a nucleic acid molecule comprising the nucleotide sequence of SEQ ID NO: 2 or a full-length complement thereof;
  b) a nucleic acid molecule encoding a polypeptide comprising the amino acid sequence of SEQ ID NO: 1 or a fragment thereof;
  c) a nucleic acid molecule encoding a polypeptide comprising an amino acid sequence having at least 90% identity to the amino acid sequence set forth in SEQ ID NO: 1 or a fragment thereof; and
  d) a nucleic acid molecule encoding a polypeptide comprising an amino acid sequence having deletions, substitutions, insertions of one or more amino acids compared with the amino acid sequence set forth in SEQ ID NO: 1 or a fragment thereof.

2. A DNA construct comprising the nucleic acid molecule of item 1.

3. The DNA construct of item 3, further comprising a nucleic acid molecule encoding a heterologous polypeptide.

4. A host cell comprising the DNA construct of item 2 or 3, said host cell is preferably bacterial cell and eukaryotic cell, more preferably plant cell and yeast cell, said plant cell is preferably Gramineous plant cell, in particular preferably rice (*Oryza sativa* L.) cell.

5. A transgenic plant comprising the host cell of item 4.

6. A transformed seed of the plant of item 5, wherein said seed comprises the DNA construct of item 2 or 3.

7. A polypeptide having insect pest-killing activity, selected from the group consisting of:
  a) a polypeptide comprising the amino acid sequence of SEQ ID NO: 1 or a fragment thereof;
  b) a polypeptide comprising an amino acid sequence having at least 90% identity to the amino acid sequence set forth in SEQ ID NO: 1 or a fragment thereof; and
  c) a polypeptide comprising an amino acid sequence having deletions, substitutions, insertions of one or more amino acids compared with the amino acid sequence set forth in SEQ ID NO: 1 or a fragment thereof; or
  d) a polypeptide encoded by the amino acid sequence set forth in SEQ ID NO:1.

8. The polypeptide of item 7, further comprising a heterologous amino acid sequence.

9. A composition comprising the polypeptide of item 7.

10. The composition of item 9, wherein said composition is selected from the group consisting of powder, fines, pellet, granule, spray, emulsion, colloid and solution.

11. The composition of item 9 or 10, comprising about 1 wt. %-about 99 wt. % of said polypeptide.

12. A method for controlling insect pest population, comprising contacting said population with pesticidally effective amount of the polypeptide of item 7.

13. A method for killing insect pest, comprising contacting or feeding said pest with pesticidally effective amount of the polypeptide of item 7.

14. A method for producing the polypeptide of item 7 having insect pest-killing activity, comprising culturing the host cell of item 4 under the condition of expressing a nucleic acid molecule encoding the polypeptide therein.

15. A plant having DNA construct stably incorporated into its genome, said DNA construct comprises a nucleotide sequence encoding a protein having insect pest-killing activity, wherein said nucleotide sequence is selected from the group consisting of:

a) a nucleic acid molecule comprising the nucleotide sequence of SEQ ID NO: 2 or a full-length complement thereof;

b) a nucleic acid molecule encoding a polypeptide comprising the amino acid sequence of SEQ ID NO: 1 or a fragment thereof;

c) a nucleic acid molecule encoding a polypeptide comprising an amino acid sequence having at least 90% identity to the amino acid sequence set forth in SEQ ID NO: 1 or a fragment thereof; and d) a nucleic acid molecule encoding a polypeptide comprising an amino acid sequence having deletions, substitutions, insertions of one or more amino acids compared with the amino acid sequence set forth in SEQ ID NO: 1 or a fragment thereof;

wherein said nucleotide sequence is operably linked to a promoter, said promoter drives the expression of an encoding sequence in plant cells.

16. A method for protecting plant against insect pest, comprising introducing at least one expression vector comprising the nucleotide sequence of item 1 into said plant or cells thereof, said nucleotide sequence encodes an insecticidal polypeptide.

17. The method of item 16, wherein said plant produces an insecticidal polypeptide having pesticidal activity against insect pest.

18. A method for improving plant stress resistance, comprising introducing at least one expression vector comprising the nucleotide sequence of item 1 into said plant or cells thereof, said nucleotide sequence encodes an insect pest-killing polypeptide.

19. A plant breeding method, comprising introducing at least one expression vector comprising the nucleotide sequence of item 1 into said plant or cells thereof, said nucleotide sequence encodes an insect pest-killing polypeptide.

20. The method according to any one of items 15-19, wherein said plant is preferably Gramineous plant, in particular preferably rice.

21. The method according to any one of items 12-19, wherein said insect pest is preferably lepidopteran pest, more preferably rice borer and *Prodenia litura*.

DETAILED DESCRIPTION OF THE INVENTION

Figure 1:
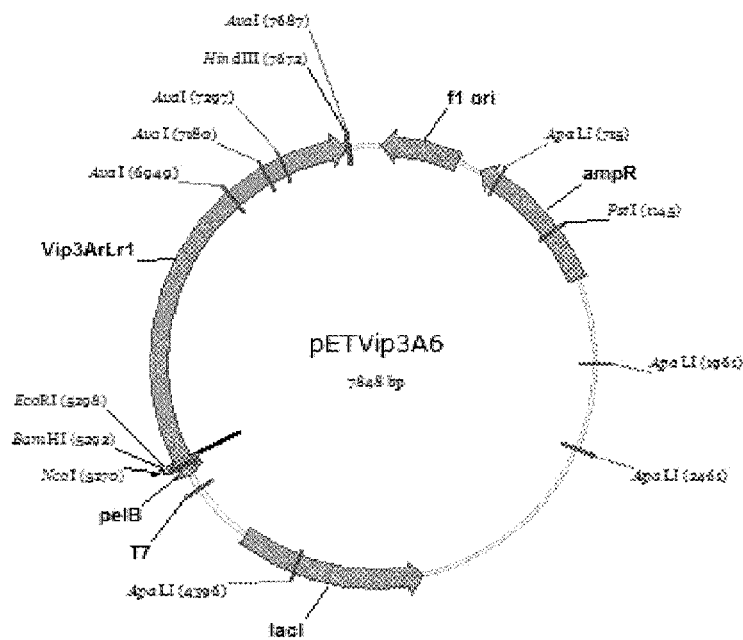
FIG. 1. The structure diagram of prokaryotic expression plasmid vector pETVip3A6.

To resolve the problems mentioned above, the inventors completed the present invention based on numerous test results. The present invention is illustrated below in detail in connection with the accompanying drawings as well as data and tables in the Examples.

To date, the Vip3 gene cloned from the natural strains of *Bacillus thuringiensis* has shown high and specific insecticidal activity against numerous pests from families, genus and species in Lepidoptera such as *Spodoptera frugiperda, Prodenia litura, Heliothis armigera* and *Pieris rapae* including cutworm, etc., but no report has ever shown that the Vip3 gene generated by these natural strains has insecticidal activity against certain lepidopteran pests such as rice *Chilo suppressalis, Tryporyza incertulas* and *Cnaphalocrocis medinalis* Guenee, etc. Fang J. et al. (2007) has reported an artificial chimeric gene Vip3AcAa that generates resistance to corn borer, which is the first evidence that the splicing of 5' end and 3' end functional domains between Vip3 genes can generate a new type of resistance. Perlak F J. et al. (1990) and Tu J. et al. (1998) have successively reported that a hybrid gene generated by Cry1Ab and Cry1Ac is able to integrate the high efficient insecticidal activity of Cry1Ab and the high insect species specificity of Cry1Ac, thus generating a better gene of Bt insecticidal protein.

The development of the Vip3 insect-resistant gene according to the present invention follows the principle of unifying protein structure and function, and the existing Vip3 protein sequence is artificially designed and modified based on the determination of its related functional domains, and eventually, gene sequences capable of producing resistance to lepidopteran pests such as rice *Chilo suppressalis* and *Cnaphalocrocis medinalis* Guenee, etc. are developed (SEQ ID NO: 1 and SEQ ID NO: 2).

An embodiment of the invention relates to a composition and method for affecting insect pests, in particular plant pests. More particularly, the nucleic acid and the fragment and variant thereof isolated according to the embodiment comprises a nucleotide sequence encoding an insecticidal polypeptide (e.g. protein). The disclosed insecticidal protein is biologically active (e.g. insecticidal) against insect pests, for example, but not limited to insect pests from Lepidoptera. Insect pests of interest include but are not limited to: rice *Chilo suppressalis, Cnaphalocrocis medinalis* Guenee, cotton *Prodenia litura*.

The composition of the embodiment comprises a nucleic acid and a fragment and variant thereof encoding an insecticidal polypeptide or a fragment thereof, expression cassette comprising the nucleotide sequence of the embodiment, an isolated insecticidal protein and an insecticidal composition. The embodiment further provides the plants and microorganisms transformed with such new nucleic acids, and the method involving the use of such nucleic acids, insecticidal composition, transformed organisms and their products for affecting insect pests.

The nucleic acid and nucleotide sequences of the embodiment may be used to transform any organism in order to produce the encoded insecticidal protein. A method involving the use of such transformed organisms for affecting or controlling plant pests is provided. The nucleic acid and nucleotide sequences of the embodiment may also be used to transform organelles.

The nucleotide sequence of the embodiment is directly useful in the method for affecting pests, in particular insect pests, e.g. lepidopteran pests. Accordingly, an embodiment provides a new method for affecting insect pests, which does not rely on the use of conventional synthetic chemical insecticides. The embodiment relates to the finding of a naturally occurring biodegradable insecticide and its encoding gene.

Numerous terms are extensively used in the following specification. The following definitions are provided to facilitate the understanding of the embodiments.

Units and symbols may be represented in their generally accepted forms. Unless otherwise indicated, nucleic acid is written from left to right in the direction of 5' to 3'; amino acid sequence is written from left to right in the direction of amino terminal to carboxy terminal. A range of numbers includes the numbers defining the range. An amino acid herein may be referred to by its generally known three-letter symbol or by its single-letter symbol suggested by the Biochemical Nomenclature Commission of IUPAC-IUB. Likewise, a nucleotide may be referred to by its generally accepted single-letter code. The foregoing terms are more comprehensively defined with reference to the specification in its entirety.

As used herein, "nucleic acid" refers to single or double stranded deoxyribonucleotide or ribonucleotide polymer.

As used herein, the term "encoding" or "encoded", when used in certain context of nucleic acid, means that a nucleic acid contains information that is sufficient to guide the translation of a nucleotide sequence into a specific protein. The information by which the protein is encoded is specified by the use of a codon. A nucleic acid encoding a protein may comprise a non-translated sequence (e.g. intron) in the translational region of the nucleic acid, or may lack such intervening non-translated sequence (e.g. as in cDNA).

The terms "polypeptide", "peptide" and "protein" may be used interchangeably herein, referring to a polymer of amino acid residues.

The terms "residue" or "amino acid residue" or "amino acid" may be used interchangeably herein, referring to an amino acid incorporated into a protein, polypeptide or peptide ("protein" in general). Amino acids may be naturally occurring amino acids, and unless otherwise noted, may include known analogs of natural amino acids, which can function in a similar manner of the naturally occurring amino acids.

The polypeptides of the embodiments may be produced by the nucleic acids disclosed herein or using standard molecular biology techniques. For example, a protein of the embodiment may be expressed in a suitable host cell by a recombinant nucleic acid of the embodiment, or may be alternatively produced by a combination of in vitro procedure followed by in vivo procedure.

Throughout the specification, the word "comprising" or its variant should be construed as an indication of including the elements, parts or steps or element groups, part groups or step groups without excluding any other elements, parts or steps or element groups, part groups or step groups.

As used herein, the term "affecting insect pests" refers to changing the ingestion, growth and/or behavior of the insect during any stage of development, including but not limited to killing the insect, delaying the growth, impeding reproductive ability, antifeedant activity, etc.

As used herein, the term "insecticidal effect", "pesticidal activity", "insecticidal activity" and "insect resistance" are used synonymously, referring to the activity of organism or substance (e.g. protein), which can be measured by, without being limited to, the mortality of pest, weight loss of pest, pest repellency and other behavioral and bodily changes in pest, after ingestion and exposure for a suitable period of time. Accordingly, an organism or substance with insecticidal activity may adversely affect at least one measurable parameter of the fitness of pest. For example, "insecticidal protein" is a protein exhibiting insecticidal activity alone or in combination with other proteins.

As used herein, the term "pesticidally effective amount" means an amount of substance or organism that having pesticidal activity when present in the environment of pests. For each substance or organism, the pesticidally effective amount is empirically determined for each pest affected in specific environment. Similarly, "insecticidally effective amount" may be used to refer to the "pesticidally effective amount" when the pest is an insect pest.

As used herein, the term "artificially designed and modified" means changes introduced (e.g. engineered) into protein structure using recombinant DNA technique, which are based upon the understanding of mechanism of protein function and the considerations of the amino acid to be introduced, deleted or substituted.

As used herein, the term "improved insecticidal activity" or "improved pesticidal activity" refers to the insecticidal polypeptide of the embodiment that has enhanced insecticidal activity with respect to the activity of its corresponding wild-type protein, and/or the insecticidal polypeptide that is effective against pests over a wider range, and/or the insecticidal polypeptide that is specific to insects that are less susceptible to the toxicity of wild-type protein. To identify an improved or enhanced pesticidal activity, it is required to show an increase in pesticidal activity against insect target of at least 10%, or at least 20%, 25%, 30%, 35%, 40%, 45%, 50%, 60%, 70%, 100%, 150%, 200% or 300% or more, with respect to the pesticidal activity of wild-type insecticidal polypeptide determined for the same insect.

For example, an improved pesticidal or insecticidal activity is provided, wherein insects over a wider or narrower range are affected by the polypeptide, with respect to the range of insects that are affected by wild-type Bt toxin. For versatility, it is desired to have an effect over a wider range, while an effect over a narrower range may also be desired when, for example, beneficial insects may be alternatively affected by the use or presence of the toxin.

With respect to the background sequence, a polypeptide encoded by a nucleotide sequence comprising mutations will comprise at least one alteration or addition of amino acid, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 35, 38, 40, 45, 47, 50, 60, 70 or 80 or more alterations or additions of amino acid. The pesticidal activity of the polypeptide may also be improved by truncating the full-length sequence, as known in the art.

In a specific embodiment, the insecticidal protein of the embodiment provides a full-length insecticidal polypeptide and a fragment thereof, and a variant polypeptide produced by a mutagenized nucleic acid designed to introduce a specific amino acid sequence into the polypeptide of the embodiment.

Mutations may be placed into any background sequence, including such truncated polypeptide, provided that it retains pesticidal activity. A skilled person in the art may easily compare 2 or more types of proteins for their pesticidal activities using measurements known in the art or described elsewhere herein. It is to be understood that the polypeptides of the embodiments may be produced by the expression of the nucleic acids disclosed herein or using standard molecular biology techniques.

Fragments and variants of the nucleotides as well as the encoded amino acid sequences and polypeptides thereof are also included in the embodiments. As used herein, the term "fragment" refers to part of the nucleotide sequence of the polynucleotide or part of the amino acid sequence of the polypeptide of the embodiment. A fragment of the nucleotide sequence may encode a protein fragment that retains the biological activity of the full-length protein and thus has pesticidal activity. As a result, it is realized that some polynucleotides and amino acid sequences in the embodiments may be properly referred to as fragments and mutants.

It is to be understood that when used to refer to a nucleic acid sequence of the embodiment, the term "fragment" also includes sequences that are useful as hybridization probes. Such nucleotide sequences usually do not encode protein fragments that remain biologically active. Therefore, a fragment of the nucleotide sequence may range from at least about 20 nucleotides, about 50 nucleotides, about 100 nucleotides and up to the full-length nucleotide sequence encoding the protein of the embodiment.

The term "variant", as used herein, refers to sequences that are substantially similar. For nucleotide sequence, conservative variants include those encoding the amino acid sequence of one of the insecticidal polypeptides of the embodiment due to the degeneracy of genetic code.

Variant nucleotide sequences also include synthetically derived nucleotide sequences that are, e.g., generated by site-directed mutagenesis, but still encode the insecticidal proteins of the embodiments. In general, the variant of a specific nucleotide sequence of the embodiment will have at least about 70%, 75%, 80%, 85%, 86%, 87%, 88%, 89%, 90%, 91%, 92%, 93%, 94%, 95%, 96%, 97%, 98%, 99% or more sequence identity to that specific nucleotide sequence. The variant of a nucleotide sequence of the embodiment may differ from the original sequence by 1-240 nucleotides, as few as 1-100, as few as 1-10, as few as 5, 4, 3, 2 or even 1 nucleotide.

An embodiment further includes a microorganism transformed with at least one nucleic acid of the embodiment, with an expression cassette comprising the nucleic acid, or with a vector comprising the expression cassette. In some embodiments, the microorganism is that propagates in plants. An embodiment provides an insecticidal composition comprising the transformed microorganism of the embodiment. In such embodiment, the transformed microorganism is typically present in the insecticidal composition in a pesticidally effective amount along with a suitable carrier. An embodiment also includes an insecticidal composition comprising an insecticidally effective amount of an isolated protein of the embodiment alone or in combination with the transformed organism of the embodiment and/or the insecticidal protein of the embodiment along with a suitable carrier.

An embodiment also includes a transformed or transgenic plant comprising at least one nucleotide sequence of the embodiment. In some embodiments, the plant is stably transformed with a nucleotide construct comprising at least one nucleotide sequence of the embodiment that is operably linked to a promoter driving the expression in plant cells. As used herein, the terms "transformed plant" and "transgenic plant" refer to a plant comprising a heterologous polynucleotide in its genome. In general, the heterologous polynucleotide is stably integrated into the genome of the transgenic or transformed plant so that being passed to successive generations. The heterologous polynucleotide may be integrated into the genome alone or as part of a recombinant expression cassette.

It is to be understood that as used herein, the term "transgenic" includes any cell, cell line, callus, tissue, plant part or plant, the genotype of which has been altered by the presence of a heterologous nucleic acid, including those transgenic organisms that are originally altered in such way and those produced by original transgenic organisms via sexual hybridization or asexual reproduction. As used herein, the term "transgenic" does not include genomic alterations (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

As used herein, the term "plant" includes whole plant, plant organ (e.g. leaf, stem, root, etc.), seed, plant cell and its progeny. A transgenic plant part falls within the scope of the embodiment and includes, e.g., plant cell, protoplast, tissue, callus, embryo as well as flower, stem, fruit, leaf and root that is derived from the transgenic plant or progeny thereof previously transformed with the DNA molecule of the embodiment and thus at least partially consists of transgenic cells.

As used herein, the term plant includes plant cell, plant protoplast, plant cell tissue culture from which the plant can be regenerated, plant callus, plant piece and plant cell that is intact in plant or plant part, such as embryo, pollen, ovule, seed, leaf, flower, branch, fruit, kernel, tassel, cob, shell, stem, root, root tip, anther, etc.

Although the embodiment is independent of specific biological mechanism for increasing plant's resistance to plant pests, the expression of the nucleotide sequence of the embodiment in plant may result in the production of the insecticidal protein of the embodiment and an increased in plant's resistance to plant pests. The plant of the embodiment is useful in the method for affecting insect pests in agriculture.

Accordingly, the protein of the embodiment can be altered in various ways, including substitution, deletion, truncation and insertion of amino acid. The method for such operation is generally known in the art. For example, a variant of the amino acid sequence of the insecticidal protein can be prepared by the introduction of mutations into the synthesizing nucleic acid (e.g. DNA molecule).

The mutagenized nucleotide sequence of the embodiment can be modified in such way in order to alter about 1, 2, 3, 4, 5, 6, 8, 10, 12 or more amino acids present in the primary sequence of the encoded polypeptide. Alternatively, even more alterations from natural sequence may be introduced in this manner so that the encoded protein may have at least about 1% or 2%, or about 3%, 4%, 5%, 6%, 7%, 8%, 9%, 10% or more alterations or codons modified otherwise, compared with the corresponding original protein.

One skilled in the art will appreciate that the addition and/or substitution of amino acid is generally based upon the relative similarity of the amino acid side chain substituents, e.g. their hydrophobicity, charge, size and so on. The exemplary amino acid substituting groups taking various aforementioned characteristics into consideration are well known to one skilled in the art, and include arginine and lysine, glutamic acid and aspartic acid, serine and threonine, glutamine and asparagine, and valine, leucine and isoleucine.

Accordingly, the gene and nucleotide sequence of the embodiment include naturally occurring sequence and the mutant. Also, the protein of the embodiment include artificially modified protein and its variant (e.g. truncated polypeptides) and modified (e.g. mutants) forms. Such variant will continue to have the desired pesticidal activity. The deletion, insertion and substitution of the protein sequence incorporated herein are not intended to bring fundamental changes to the characteristics of the protein. However, if the precise role of the substitution, deletion or insertion can not be predicted, one skilled in the art will recognize that it will be evaluated by conventional screening assays, such as insect ingestion assay.

The variant nucleotide sequence and protein also include sequence and protein derived from mutagenesis and recombination procedures such as DNA shuffling. Through such procedure, one or more different encoding sequences can operate to produce the new insecticidal protein with desired properties. In this way, a recombinant polynucleotide library is generated by the population of polynucleotides comprising corresponding sequences of sequence regions that have substantial sequence identity and may be recombined homologously in vitro or in vivo. For example, by using this method, full-length encoding sequence, sequence motif encoding domain of interest, or any fragment of the nucleotide sequence of the embodiment may be shuffled between the nucleotide sequence of the embodiment and corresponding section of other known nucleotide sequence of Vip to obtain a new gene encoding a protein having improved properties of interest.

An embodiment further relates to plant propagating materials of the transformed plant of the embodiment, including but not limited to seeds, tubers, corms, bulbs, leaves and cutting woods of roots and branches.

The embodiment can be used to transform any plant species, including but not limited to monocotyledons and dicotyledons.

The composition of the embodiment is useful for protecting plant, seed and plant product in a variety of ways. For example, the composition may be used in the method involving placing effective amount of insecticidal composition into the environment of pests, which can be done by processes selected from spraying, dusting, broadcasting or seed coating.

Before the plant propagating materials (fruit, tuber, bulb, corm, grain, seed), in particular, seeds, are commercially marketed, they are routinely treated with protective coating including herbicide, insecticide, fungicide, bactericide, nematocide, molluscicide or the combination of several of these agents, and if necessary, in combination with further carrier, surfactant or application facilitating adjuvant that is routinely employed in the field of formulation, to provide protection against damages caused by bacteria, fungi or animal pests. For seed treatment, the tuber or grain is impregnated by liquid formulation or coated by combined wet or dry formulation. Protective coating can be applied on the seed. Furthermore, in specific scenario, other applications for plant are possible, for example, the treatment for bud or fruit.

A gene encoding the insecticidal protein of the embodiment can be introduced into a microorganism host via a suitable vector, and the host is applied on environment, or plant or animal. In the context of inserting nucleic acid into cell, the term "introduced" means "transfected" or "transformed" or "transducted", and includes incorporating the nucleic acid mentioned into eukaryotic or prokaryotic cell, wherein the nucleic acid can be incorporated into the cell's genome (e.g. chromosomal, plasmid, plastid or mitochondrial DNA), becoming autonomous replicon or transient expression (e.g. transfected mRNA).

Many methods can be used to introduce a gene expressing an insecticidal protein into a microorganism host under conditions allowing stable maintenance and expression of the gene. For example, an expression cassette comprising the nucleotide construct of interest that is operably linked to the transcription and translation regulatory signals for expressing the nucleotide construct, and the nucleotide sequence that is homologous to the sequence in the host organism whereby integration will occur, and/or the replication system working in the host whereby integration or stable maintenance will occur, may be constructed. The transcription and translation regulatory signals include but not limited to promoter, transcription initiation site, operator gene, activator, enhancer, other regulatory element, ribosome binding site, start codon, stop signal, etc.

In an embodiment, a transformed microorganism (which may comprise intact organisms, cells, one or more spores, one or more insecticidal proteins, one or more insecticidal components, one or more pest affecting components, one or more mutants, live or dead cells and cell components including the mixture of live and dead cells and cell components, and fragmentized cells and cell components) or an isolated insecticidal protein can be formulated in combination with acceptable carriers as one or more insecticidal compositions, such as, for example, suspension, solution, emulsion, dusting powder, dispersible granule or pellet, wettable powder and emulsifiable concentrate, aerosol or spray, impregnated granule, adjuvant, coatable paste, colloid and for example, encapsulation of polymeric substances. Such formulated composition may be prepared by conventional methods such as dehydration, lyophilization, homogenization, extraction, filtration, centrifugation, sedimentation or concentration of cell culture containing polypeptides.

Such composition disclosed above can be obtained by the addition of surfactant, inert carrier, preservative, humectant, ingestion stimulant, attractant, encapsulating agent, adhesive, emulsifier, dye, UV protective agent, buffer, flow agent or fertilizer, micronutrient donor or other formulations affecting plant growth. The one or more agrochemicals include, but not limited to, herbicide, insecticide, fungicide, bactericide, nematocide, molluscicide, acaricide, plant growth regulator, defoliant (harvest aid) and fertilizer, and can be combined with carriers, surfactants or adjuvants or other components that are routinely employed in the field of formulation in order to facilitate product processing and apply on specific target pests. The suitable carrier and adjuvant may be solid or liquid, and correspond to the substances that are routinely employed in formulating technique, for example, natural or regenerated mineral, solvent, dispersant, humectant, viscosity increaser, adhesive or fertilizer. The active ingredient of the embodiment is normally applied in the form of a composition, and can be applied on crop area, plant or seed to be treated. For example, the composition of the embodiment can be applied on cereals for preparing a granary or cellar and the like, or on cereals being stored in a granary or cellar and the like. The composition of the embodiment may be applied with other compounds, either concurrently or sequentially. The method applying the active ingredient of the embodiment or the agrochemical composition of the embodiment comprising at least one insecticidal protein produced by the bacterial strain of the embodiment, includes but not limited to leaf application, seed coating and soil application. The number and ratio of application depend on the infestation intensity by respective pest.

The composition of the embodiment may be used in direct application in a suitable form or as a concentrate of the basal composition, which requires dilution with appropriate amount of water or other diluent prior to the application. The pesticidal concentration will vary depending on the nature of specific formulation, particularly depending on whether it is a concentrate or to be used directly.

The composition comprising the transformed microorganism and insecticidal protein of the embodiment may be applied in the environment of insect pests by, for example, spraying, atomizing, dusting, sowing, coating or pouring, introducing into or on the soil, introducing into irrigation water, by seed treatment or general application or dusting when pests have started to emerge or, as a protective measure, prior to their emergence. For example, the insecticidal protein and/or transformed microorganism of the embodiment may be mixed with cereal to protect it in storage. In general, it is important to have pests well controlled during the early stage of plant growth, since this is the most vulnerable period. The composition of the embodiment may easily comprise another insecticide, if necessary. In one embodiment, the composition comprising a carrier and the dead cells of a *Bacillus* strain or transformed microorganism of the embodiment, is applied directly in the soil in its granulated form at the time of planting.

Another embodiment is the granulated form of the composition comprising agrochemicals such as herbicide, insecticide, fertilizer, inert carrier, and the dead cells of a *Bacillus* strain or transformed microorganism of the embodiment.

One skilled in the art will appreciate that not all the compounds are equally effective against all the pests. The compounds of the embodiment have shown activities against insect pests that may include those economically important pests in agronomy, forest, greenhouse, nursery, ornamental plants, food and fiber, public and animal health, household and commercial structure, household and storage product.

A variety of bioassay techniques are known to one skilled in the art. The general procedure comprises adding the experimental compound or organism into the food source in a sealed container. The pesticidal activity can be measured by, without being limited to, the change in mortality, weight loss, attraction, repellency and other behavioral and bodily changes after ingestion and exposure for a suitable period of time. The bioassay described herein may be used for any ingesting insect pest at larval or adult stage.

EXAMPLES

All the molecular biology techniques and methods used in the following examples of the present invention are those relatively mature at present. Most of them are the core techniques frequently used in our laboratory, in addition, these techniques are described in detail in both Current Protocols in Molecular Biology and Molecular Cloning: A Laboratory Manual, etc. The following examples are presented to illustrate rather than limit the present invention.

Example 1

Prokaryotic Expression and Extraction of Inclusion Body

The improved Vip3 encoding sequence was constructed into the prokaryotic expression vector pET22b (FIG. 1), and the prokaryotic expression and extraction of inclusion body were preformed using *E. coli* DH5α strain. Detailed steps were as follow: a monoclonal colony was cultured overnight in small amount of medium, and then scaled up to 50 ml and cultured until $OD_{600}$ of 0.4-0.6; 1 ml culture was centrifugated at 13000 rpm for 1 min and harvested, then dissolved with 30 µl water; IPTG was added to 1 mM, followed by a 6-hr further culture; the culture was then centrifuged at 4° C. and 8000 rpm for 10 min, with the supernatant removed; the pellet was resuspended in 10 ml 1×PBS, and 10 mg lysozyme was added to treat at 25° C. for 30 min; then protease inhibitor PMSF was added to a final concentration of 1 mM, and ultrasonic disruption was carried out on ice (200 W, 30S sonication, 30 s interval, 30 cycles); then TritonX-100 was added to a final concentration of 1%, and mixed at room temperature for 30 min, followed by a 10-min centrifugation at 4° C. and 12000 rpm; the pellet collected in centrifugation was then washed once with inclusion body protein purification buffer, and then resuspended in ⅟₅₀ bacterial liquid of inclusion body protein purification buffer, lysozyme was added at 1 mg/ml, and a 25° C. water bath was carried out for 30 min; then PMSF was added to 1 mM, and ultrasonic disruption was carried out at 800 W for 10 min; subsequently, *E. coli* DNA was cleavaged with Nuclease Si, and a centrifugation was carried out at 4° C. and 5000 rpm for 10 min, after the removal of the supernatant, the pellet was washed with 25 ml inclusion body protein purification buffer for 3 times, and the resulting inclusion body was then stored in −20° C. freezer until use.

Example 2

Insect Resistance Identification of Vip3 Protein

The insect resistance identification of Vip3 protein was carried out according to artificial feeding method. The artificial feed used in insect growing was formulated with reference to the formula invented by Lanzhi Han, Maolin Hou, Yufa Peng et al. (2009). For inoculation, the feed was cut into 2 cm squares or the prepared artificial feed was put into a 24-well plate when it was not cooled down. Meanwhile, each inclusion body protein sample to be tested was diluted to 640 µg/ml according to the lethal dose for the target pest that was determined by the preliminary experiment, then 100 µl was taken and applied on the feed, then air dried. Five insects were applied per feed piece in triplicate. Then, it was covered with semi-permeable membrane, and continuously recorded for 7 days, so as to observe their survival status. Test results indicated that the Vip3 protein expressed by the new encoding sequence exhibited good insecticidal effect on *Chilo suppressalis*: in 45 3rd-instar larvae of *Chilo suppressalis* in total that were fed with said protein in 3 repetitions, 33 were dead and 12 survived, and the average mortality upon statistical treatment was 0.73±0.11; while the mortalities for larvae of *Chilo suppressalis* that were repeatedly fed with empty plasmid vector extract, protein dilution buffer and clean water control, were only 0.20±0.00, 0.15±0.07 and 0.20±0.00, respectively. Similar results of experiment were also observed in the feeding of *Prodenia litura*, with a better performance on insect resistance: the mortality for the fed larvae of *Prodenia litura* was 0.95±0.12. The results therefore demonstrated that the new Vip3 protein developed not only produces resistance to rice *Chilo suppressalis*, but is also of high resistance to cotton *Prodenia litura* like many other natural Vip3 proteins. This is heretofore the first Vip3 new gene with insect resistance to rice *Chilo suppressalis*, which is not found in nature but from improved design.

Further sequence alignment analysis indicated that the artificially designed and synthesized new VIP3A protein has up to 93% sequence identity to the known VIP3A-class insecticidal protein, and thus its gene may belong to the class of Vip3A in classification. Additionally, taking into account that the improved design of the protein results in the generation of resistance to rice lepidopteran pests such as *Chilo suppressalis*, to this end, the gene producing the protein was officially named Vip3ArLr1(Vip3A class and rice Lepidoptera resistance).

Example 3

Construction of Vip3ArLr1 *Agrobacterium* Plasmid Vector and *E. coli* Transformation The plasmid used in this example for the construction of Vip3ArLr1 *Agrobacterium* plasmid vector is pSB130actin-nos (an empty vector engineered in our laboratory), which consists of double transfer DNA (T-DNA) regions. The purpose of constructing a double T-DNA plasmid vector is to allow the gene of interest and marker gene, after transforming the rice, to have a chance to integrate separately into the acceptor's genome, in order to facilitate the separation and removal of the marker gene in the subsequent segregating generations by means of selfing. The promoter driving the expression of the gene of interest is rice actinI promoter, 0.839 kb in size, the donor of which is rice; and the terminator is the artificially synthesized nosT, 0.271 kb in size, which is used to terminate the transcription and conduct the polyadenylation of messenger RNA (mRNA) (Fraley et al, 1983); the marker gene used in the screening of plasmid itself is kanamycin resistant gene, kan+.

Figure 2:
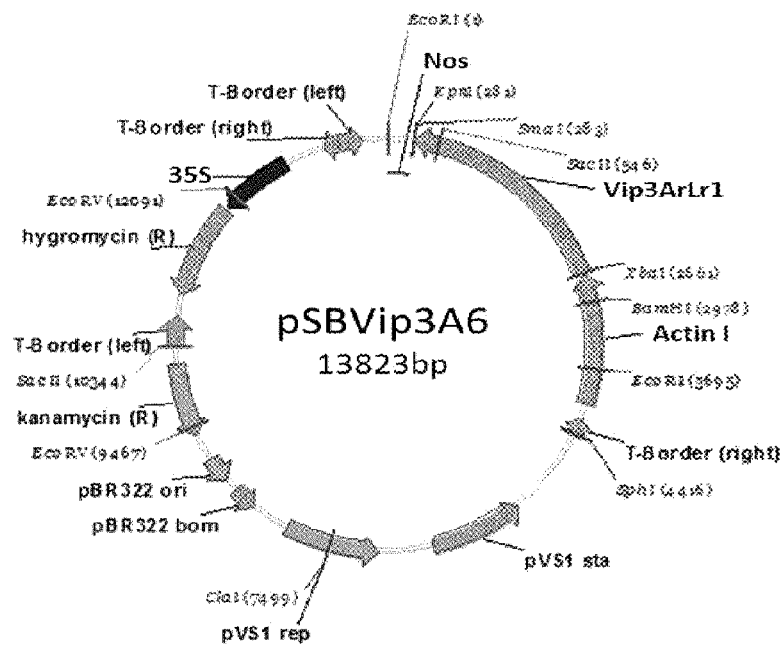
FIG. 2. The structure diagram of *Agrobacterium* plasmid vector pSBVip3A6.

The marker gene used to screen for transformant is hygromycin phosphotransferase gene (hph), 1.026 kb in size, the donor organism of which is *E. coli*. The marker gene was constructed in a T-DNA region different from that of the gene of interest when the vector was designed. The plasmid vector constructed is named pSBVip3A6, the structure diagram of which is shown in FIG. 2.

The detailed steps for constructing Vip3ArLr1 plasmid vector were as follow:

3.1 Preparation of Vip3ArLr1 Linking Fragment

The Vip3ArLr1 linking fragment was obtained by amplification from pET11a prokaryotic expression vector using PCR technique. During the amplification, restriction sites that will ligate to the multiple cloning sites of the *Agrobacterium* plasmid vector in the next step were introduced. The primers and reaction system of the PCR amplification used can be found in Table 1. The PCR reaction program used is: denaturation at 94° C. for 5 min, followed by 35 cycles of: denaturing at 95° C. for 15 sec, annealing at 55° C. for 30 sec and elongating at 72° C. for 2 min, and incubation to store at 10° C. after elongating at 72° C. for another 10 min.

TABLE 1

| PCR reaction system | |
| --- | --- |
| Component | Volume (μl) |
| 10× PCR buffer | 2.5 |
| 2.5 mM dNTP | 2.0 |
| Taq enzyme | 0.2 |
| Primer 1 | 0.25 |
| Primer 2 | 0.25 |
| Template | 1.0 |
| Double distilled water | 18.8 |
| Total | 25.0 |

Once the amplification was completed, the PCR products were separated by electrophoresis using 1% agarose gel, and the DNA fragment of interest was recovered according to the instruction of Gel Extraction Kit from Axygen. The detailed procedures were as follow: the DNA fragment of interest was cut out from the agarose gel under UV light, blotted with absorbent paper to remove the liquid on the surface, and minced and put into a 1.5 ml centrifuge tube. The gel was weighed on a balance and the weight value obtained was used as one gel volume (e.g. 100 mg=100 μl); 3-fold gel volume of DE-A buffer was added into the centrifuge tube, which was placed on a thermostatic shaker at 72° C., 250 rpm for 15 min; after the gel was melted, another 1.5-fold gel volume of DE-B buffer was added, and mixed well; the mixture above was transferred to a DNA preparation tube (placed in a 2 ml centrifuge tube), followed by a centrifugation at 12500 rpm for 1 min, with the supernatant discarded; 500 μl washing buffer W1 was added, followed by a centrifugation at 12500 rpm for 1 min, with the supernatant discarded; 700 μl washing buffer W2 was added, followed by a centrifugation at 12500 rpm for 1 min, with the supernatant discarded, repeating said step once; a further centrifugation at 12500 rpm was carried out for 1 min; 25 μl preheated deionized water at 60° C. was added to the center of the DNA preparation membrane. The DNA was collected by centrifugation, and stored at −30° C.

3.2 Double Digestion of the Purified Vip3ArLr1 DNA Fragment and *Agrobacterium* Double T-DNA Plasmid (pSB130actin-Nos) Fragment Double digestion was performed with XbaI and SmaI restriction endonucleases on purified Vip3ArLr DNA fragment and *Agrobacterium* double T-DNA plasmid (pSB130actin-nos) fragment. See Table 2 for the digestion reaction system.

TABLE 2

| Digestion reaction system | |
| --- | --- |
| Component | Volume (μl) |
| XbaI | 1.0 |
| SmaI | 1.0 |
| 10× M buffer | 2.0 |
| Plasmid DNA/PCR product | 6.0 |
| Double distilled water (d$_2$H$_2$O) | 10.0 |
| Total | 20.0 |

After double digestion, PCR products were purified with AxyPrep PCR Clean-up Kit from Axygen, and the steps were as follow: in the PCR reaction solution, 3-fold volume of PCR-A buffer (if PCR-A buffer was less than 100 μl, it was added to 100 μl) was added; the reaction solution was mixed well and transferred to a preparation tube. The preparation tube was placed in a 2 ml centrifuge tube, and centrifugated at 12000 rpm for 1 min, with the supernatant discarded; the preparation tube was put back into the 2 ml centrifuge tube, wherein 700 μl washing buffer W1 (prior to use, it must be ensured that anhydrous ethanol was added into the washing buffer W1 by the specified volume on the reagent bottle) was added, and centrifugated at 12000 rpm for 1 min, with the supernatant discarded; the preparation tube was put back into the 2 ml centrifuge tube, wherein 400 μl washing buffer W2 was added, and centrifugated at 12000 rpm for 1 min (this step was optional, and when taking out the 2 ml centrifuge tube from the centrifuge, the washing buffer W2 on the bottom of the tube shall not contact with the preparation tube); the preparation tube was placed in a clean 1.5 ml centrifuge tube (provided in the kit), and 25-30 μl deionized water was added to the center of the membrane in the preparation tube, then it was allowed to stand at room temperature for 1 min, and centrifuge at 12000 rpm for 1 min, in order to elute the DNA and move to the next step.

3.3 Ligation of Vip3ArLr1 DNA Fragment and *Agrobacterium* Double T-DNA Plasmid (pSB130actin-Nos) Fragment First, the concentrations of the recovered vector fragments and the gene of interest were determined. Then, the recovered vector fragments and the gene of interest were added into a 50 μl sterile centrifuge tube in a 1:3 ratio, and ligated overnight at 4° C., see Table 3 for the ligation system used.

TABLE 3

Ligation system

| Component | Volume (μl) |
|---|---|
| PCR product | 9.5 |
| Plasmid DNA | 3.0 |
| T4 ligase | 1.0 |
| 10× T4 ligation buffer | 1.5 |
| Total | 15.0 |

3.4 *E. coli* Transformation

The strain used as cloning recipient in the present invention was *E. coli* strain DH5α, and heat-shock protocol was used for transformation. Detailed procedures of transformation were as follow: 10 μl ligation product was pipetted into 80 μl *E. coli* DH5α competent cells, pipetted up and down until well mixed, and placed on ice bath for 30 min. After heat shock at 42° C. for 90 s, it was quickly put back on ice bath and allowed to stand for 2 min; 1 ml LB liquid medium was then added into each tube, and shaken at 250 rpm for 1 h on a 37° C. thermostatic shaker; once the bacterial solution was recovered, a centrifugation was carried out and 800 μl supernatant was removed. The remaining 200 μl supernatant was well mixed with the pellet, evenly plated on the surface of LB solid screening medium (50 mg/l kanamycin), and incubated overnight at 37° C.

3.5 Identification of Positive Colonies

A transparent single colony was picked with a toothpick, and put in the PCR reaction system as the template for amplification identification. Both the PCR reaction system and reaction program are the same as above. The colonies identified as positive by PCR were picked to grow in shake culture. The plasmid was extracted with Plasmid MiniPrep Kit from Axygen, and validated by digestion. After the result was confirmed, another 10 μl plasmid was taken and sent to Invitrogen (Shanghai) for further sequencing validation. The construction of Vip3ArLr1 vector plasmid was considered as complete once the result was confirmed.

Example 4

*Agrobacterium*-mediated Genetic Transformation 4.1 *Agrobacterium* Transformation of Vip3ArLr1 Vector Plasmid

*Agrobacterium* transformation of Vip3ArLr1 vector plasmid was performed by electroporation, wherein the *Agrobacterium* strain used was EHA105. Detailed procedures were as follow: 0.5 μl Vip3ArLr1 vector plasmid was taken and added into a 1.5 ml centrifuge tube containing 60 μl *Agrobacterium* EHA105 electroporation competent cells, mixed well by pipetting up and down, then transferred to a cuvette; immediately after electroporation, 1 ml LB liquid medium was added, pipetted up and down to mix well and then transferred into the previous 1.5 ml centrifuge tube for a 1-hr shake culture on a 28° C. thermostatic shaker; after the bacterial liquid was recovered, 100 μl liquid was pipetted and evenly plated on the surface of LB solid screening medium (containing 50 mg/l kanamycin, 25 mg/l rifampicin), and then cultured at 28° C. for 2 days; once the colony was validated as positive clone by PCR, the positive clone was shake cultured and the bacterial liquid was stored (50% glycerol concentration, stores at −80° C.) until use.

4.2 Rice Transformation

The rice transformation was performed according to the method described in Qiaoquan Liu et al. (2004). The detailed procedures were as follow: 200 μl *Agrobacterium* liquid stored at −80° C. was pipetted, and evenly plated on the surface of LB solid medium containing 25 mg/l rifampicin and 50 mg/l kanamycin, and then cultured overnight at 28° C.; a single colony was picked to scale up the culture with the same liquid medium; 200-300 μl fresh bacterial liquid was pipetted to inoculate into 20 ml LB liquid medium containing 25 mg/l rifampicin and 50 mg/l kanamycin, and cultured at 28° C. with shaking (220 rpm) for 16-18 h. Sufficient amount of bacterial liquid was taken and centrifugated at 4000 rpm for 15 min, with the LB medium supernatant discarded; 20 ml 0.1 M $MgSO_4$ solution was added to resuspend the *Agrobacteria* (pipetting up and down gently), followed by a centrifugation at 4000 rpm for 10-15 min, with the $MgSO_4$ supernatant containing antibiotics discarded; 5 ml AA-AS infection medium, which contains 200 μM acetosyringone (AS), was added to resuspend the *Agrobacteria*, then AA-AS infection medium (q.s.) was added to adjust the $OD_{600}$ of the bacterial liquid to 0.8-1.0; once the concentration was adjusted, aliquots of 20-25 ml/tube were distributed in sterile 50 ml centrifuge tubes, until use.

The embryogenic callus of *Oryza sativa L. japonica.* cv. Nipponbare ("Nipponbare") precultured for around 7 days was transferred from subculture Petri dish to an empty dish covered with sterile filter paper, air dried on super clean bench for around 10-15 min, during which the callus was slowly flipped with a sterilized spoon to allow it completely dry; after dry, it was transferred to a centrifuge tube filled with bacterial liquid, gently shaken (not too vigorously) for 40 min at room temperature, and the centrifuge tube was allowed to stand for 10 min on the super clean bench; the bacterial liquid was discarded, and the embryogenic callus was placed on sterile filter paper to dry for around 15 min; subsequently, the embryogenic callus was transferred to CC-AS co-culture medium containing 200 μM acetosyringone, which was covered with sterile filter paper on the surface, and cultured in dark at 28° C. for 50-55 h; the embryogenic callus that has few *Agrobacteria* grown on the surface or is not contaminated was selected, transferred to N6 bacteriostatic medium containing 2.0 mg/L 2,4-D, and 500 mg/l cephamycin, and cultured bacteriostatically in darkroom at 28° C. for 3-4 d; the bacteriostatically cultured callus was transferred to N6 screening medium containing 500 mg/l cephamycin and 65 mg/L hygromycin, and cultured in darkroom at 28° C.; in the first week, the contamination of the *Agrobacterium* was checked daily. If the contamination was out of control, the screening medium must be replaced timely. Every half month, well-growing callus was selected to subculture on fresh screening medium, and the concentration of cephamycin in the medium was adjusted based on the level of self-contamination of the *Agrobacterium*. In general, the concentration might be halved by the third or fourth round of subculture screening.

According to the procedures above, 3 repeated transformations were carried out, resulting in 35 independent transformants obtained from 101 callus for transformation.

4.3 PCR Identification of Transgenic Resistant Callus 4.3.1 Extraction of Resistant Callus Genome DNA 0.2-0.3 g transgenic resistant callus from each subcultured independent transformant was taken, and placed in mortar that was washed and sterilized by alcohol burning. 600 μl of 1.5×CTAB extraction buffer was added to grind until homogenized. The homogenate was transferred into a 1.5 ml centrifuge tube, which was then placed on 60° C. water bath for 25 min (repeatedly inverted twice during the process). Next, 400 μl chloroform was added, and the centrifuge tube was inverted upside down for several times till thoroughly mixed, and centrifugated for 6 min (13000 r/min); 400 μl of the supernatant was pipetted into a new centrifuge tube, to which 800 μl anhydrous ethanol was added, and the resulting solution was mixed well. The centrifuge tube was placed at −30° C. for more than 30 min, centrifugated at 13000 rpm and room temperature for 5 min, with the supernatant discarded. The DNA pellet was rinsed with 75% ethanol, placed at room temperature to dry after the ethanol was removed, and then dissolved in 100 μl sterile water for overnight.

4.3.2 PCR Detection of Vip3ArLr1 in Transgenic Resistant Callus

Molecular detection of Vip3ArLr1 in transgenic resistant callus was performed using conventional PCR technique. The primers used for detection were: vip-F, 5'-GCTGT-TATG CGGCCATTGTC-3' (SEQ ID NO: 3) and vip-R, 5'-GACGTCTGTCGAGAAGTTTC-3' SEQ ID NO: 4). The amplified fragment of interest was about 300 bp in size. See Tables 3-4 for the PCR reaction system. The PCR reaction program used was: denaturation at 94° C. for 5min, followed by 35 cycles of: denaturing at 95° C. for 15 sec, annealing at 55° C. for 30sec and elongating at 72° C. for 30 sec, and incubation to store at 10° C. after elongating at 72° C. for another 10 min. The resulting PCR amplification products was separated by electrophoresis with 0.8% agarose gel, photographed and then stored.

Figure 3:
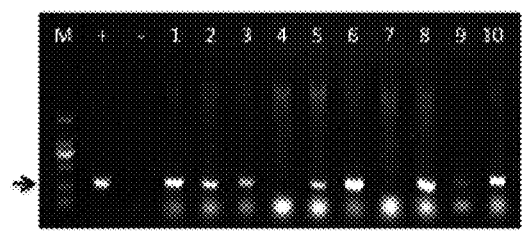
FIG. 3. PCR detection of Vip3ArLr1 in transgenic resistant callus. In the figure, M: molecular weight marker; +: plasmid positive control; −: empty plasmid negative control; 1-10: transformed callus; the arrow points to the target band.

Test results indicated that 30-70% of the transgenic resistant callus screened from the 3rd-4th round were Vip3ArLr1 positive (FIG. 3), showing that the gene of interest was integrated into the recipient cell.

4.4 Differentiation of Vip3ArLr1 Positive Callus

The differentiation of Vip3ArLr1 positive callus was performed according to the method described by Yang R et al. (2011). The detailed procedures were as follow: the resistant callus that was positive for the gene of interest Vip3ArLr1 was transferred to $N_6$ differentiation medium (N6 minimal medium+2 mg/l Kinetin+1 mg/l NAA+4% Gelrite), pre-differentiated in darkroom at 28° C. for 7-9 days, and then transferred to fresh differentiation medium for the differentiation of plantlet in light room at 25° C. (green spot can usually be observed after 7-14 days, and it can differentiate into plantlet after 3 weeks). After washing off the medium adhered to the root system, the plantlet obtained was then transferred into Yoshida medium, either directly (root-bud simultaneous differentiation type) or after strengthening the root in rooting medium (bud-first differentiation type), for transitional culture. Once the growth was good and stable, it was then transplanted into greenhouse until mature.

Example 5

Detection of Vip3ArLr1 Protein in Positive Transgenic Plant

The Vip3ArLr1 protein in positive transgenic plant was detected and analyzed with Vip Test strips obtained from Youlong Biotech Co. Ltd, Shanghai. The extraction of protein from rice leaf and the detection using test paper were performed according to the steps described in the product manual.

The detailed procedures were as follow: the leaf of transgenic rice that is around 2-3 cm in length was taken and put in a mortar, into which 1 ml distilled water or commercially available pure water was added. After finely grinding, it was pipetted into a 1.5 ml centrifuge tube, followed by a centrifugation at 12000 rpm for 30 s. The supernatant was then transferred into another 1.5 centrifuge tube. Then the test strip was added, and its color development was observed after 5 min.

Figure 4:
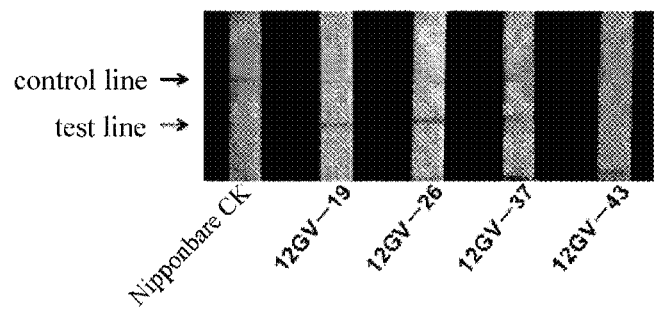
FIG. 4. Detection result of Vip3ArLr1 protein. In the figure, 12GV-19, 12GV-26, 12GV-37 and 12GV-43 are independent transformed lines of Vip3ArLr1.

The results showed that there were target bands in all the protein samples of the positive transgenic plant (FIG. 4), although the intensity of the detection signal varied in different transformants, which indicated, on one hand, that Vip3ArLr1 gene can be normally expressed in the recipient genome, and on the other hand, that the expression level of Vip3ArLr1 protein in different transformants (such as 12GV-26 and 12GV-43 in FIG. 4) may vary significantly due to the different insertion sites or the difference in copy numbers.

Example 6

Identification of Insect Resistance of Vip3ArLr1 Transgenic Line

The plant materials used in insect inoculation were the independent transformed lines that are positive in the DNA and protein detections described above. Both naturally occurring infection and artificial insect inoculation were employed in the insect inoculation identification, and the indicators of which were dead heart rate, rate of white ear, rate of roll leaf and average corrected mortality. Naturally occurring infection identification was performed primarily against *Cnaphalocrocis medinalis* Guenee, and artificial insect inoculation identification was performed against *Chilo suppressalis* and *Cnaphalocrocis medinalis* Guenee. Artificial insect inoculation identification includes detached leaf inoculation, detached stem inoculation, single plant insect resistance identification, and field artificial insect inoculation.

Detached leaf inoculation: at the mid-tillering stage of rice, 3 pieces of leaves of 3~4 cm in length from different tillering flag leaves on the rice plant of each test line material were randomly obtained by cutting, with 3 plants repeatedly identified per test line material. Then small pieces of filter paper impregnated with 0.1 g/l benzimidazole preservative solution were placed on the top of both ends of the leaf. The treated leaf was transferred into a small flat-bottom glass test tube with a length of 9.5 cm and an inner diameter of 1.5 cm. Then 12 1st instar larvae of *Chilo suppressalis* or *Cnaphalocrocis medinalis* Guenee were placed in each tube. The tube was plugged with absorbent cotton, and incubated at 28° C. under light for growing. After 4 days, 2~3 fresh test leaves were added to the tube. The survival of test larvae was examined, recorded and calculated after 7 days, and thus the mortality of test larvae for each test line material was calculated. Then the corrected mortality of test larvae for each test line material was calculated with reference to the average mortality of test larvae for insect-susceptible controls using the following equation: corrected mortality %=(mortality of test larvae for test line material−average mortality of test larvae for insect-susceptible controls)/(1−average mortality of test larvae for insect-susceptible controls)×100. Then the test material was evaluated for its resistance to target pests, i.e. *Chilo suppressalis* and/or *Cnaphalocrocis medinalis* Guenee, according to the grading standards of insect resistance identification using detached leaf inoculation, as listed in Table 4.

TABLE 4

Grading standards of insect resistance identification using detached leaf inoculation:

| Corrected Mortality % | Grading of Resistance, susceptibility |
|---|---|
| 85~100 | HR (high-resistant) |
| 60~85 | R (insect-resistant) |
| 20~60 | MR (mid-resistant) |
| <20 | S (insect-susceptible) |

Detached stem inoculation: 2 primary tillering rice seedlings were taken at their active tillering stage from each test line material, dried up and truncated into 2 stems (5 cm in length) comprising node and leaf sheath. Then small pieces of filter paper impregnated with 0.1 g/l benzimidazole preservative solution were placed on the top of both ends of the stem. The treated stem was transferred into a small flat-bottom glass test tube with a length of 9.5 cm and an inner diameter of 1.5 cm. Then 12 1st instar larvae of Chilo suppressalis were placed in each tube. The tube was plugged with absorbent cotton. After 3 days, small pieces of filter paper impregnated with 0.1 g/l benzimidazole preservative solution were added at both ends of the stem to ensure that the stem was moist. After 7 days, the stem was peeled to examine and record the number of survived larvae. The live larvae in each glass tube were weighed, if necessary. The evaluation standards are the same as those of detached leaf inoculation.

Single plant insect resistance identification: the test rice plants with 2 tillers were transplanted in plastic buckets, inoculated with 10 1st instar larvae of Chilo suppressalis for each plant, and placed under plastic net (diameter: 12 cm, height: 70 cm). After 2 weeks, the net was removed, and 20 plants per test material were repeatedly identified. On Day 15 and Day 30 after insect inoculation, the dead heart phenotype for the affected rice plant of each test line material was investigated, and the corrected dead heart rate % for test line material was calculated based on the equation below: dead heart rate % of test line material=(dead heart rate of test line material−dead heart rate of insect-susceptible control)/(1−dead heart rate of insect-susceptible control)×100.

Field artificial insect inoculation: primarily performed at both tillering stage and booting stage. The former was carried out by inoculating with 2nd instar larvae of Chilo suppressalis when the height of seedling is about 15 cm, and the latter was carried out by inoculating with newly-hatched larvae 7-10 days before earing (15 larvae/plant, 10-30 plants/line, in triplicate). The dead heart rate and rate of white ear were investigated 15-21 days after inoculation, so as to evaluate the field insect-resistant effect of the transferred gene.

Test results demonstrated that the 4 independent transformed lines of Vip3ArLr1 and their respective sister lines showed high resistance to both artificially inoculated Chilo suppressalis and naturally occurring Cnaphalocrocis medinalis Guenee. As shown in Table 4-2 to Table 4-5, the rates of white ear for the 4 independent transformed lines of Vip3ArLr1 affected in 2012 by the artificially inoculated 2nd instar larvae of Chilo suppressalis are all significantly lower than that for the affected transformed line of control gene Vip3Aa1, wherein, the rate of white ear is 0 for the first 3 transformed lines, and 6.64% for the fourth one (Table 5). The repeated identification was performed in 2013, using the leaves, stems and plants from the sister lines of the independent transformed lines described above, and the parent lines and insect-susceptible control lines were added. The Chilo suppressalis inoculated has an average corrected mortality that is lower than or slightly higher than that of Nipponbare control and the transformed line of Vip3Aa1 on the leaves and stems of 13GV-38, the sister line of one independent transformed line, and has an average corrected mortality that is over 66% on all other three transformed lines, which is significantly higher than the average corrected mortality on parent and insect-susceptible control lines (Tables 6 and 7); the dead heart rates caused by the Chilo suppressalis inoculation on plants of the 4 independent transformed lines of Vip3ArLr1 are also all significantly lower than that on the affected transformed line of control gene Vip3Aa1 (Table 8).

TABLE 5

Identification of resistance to artificially inoculated Chilo suppressalis for Vip3ArLr1 and control Vip3Aa1 transformed lines (2012).

| Transformed line | Gene | Rate of white ear (%) |
|---|---|---|
| 12GV-3 | Vip3Aa1 | 33.3 |
| 12GV-19 | Vip3ArLr1 | 0 |
| 12GV-26 | Vip3ArLr1 | 0 |
| 12GV-37 | Vip3ArLr1 | 0 |
| 12GV-43 | Vip3ArLr1 | 6.64 |

TABLE 6

Identification of resistance to artificially inoculated Chilo suppressalis for the leaves of Vip3ArLr1 and control Vip3Aa1 transformed lines (2013).

| Transformed line | Gene | Corrected mortality % for each plant line | | | Average corrected mortality % | Resistance rating |
|---|---|---|---|---|---|---|
| | | 1 | 2 | 3 | | |
| Nipponbare | Parent control | 51.6 | 61.3 | 61.3 | 58.07 ± 5.60 | MR |
| 13GV-1 | Vip3Aa1 | 61.3 | 51.6 | 51.6 | 54.83 ± 5.60 | MR |
| 13GV-12 | Vip3ArLr1 | 80.6 | 80.6 | 90.4 | 83.87 ± 5.66 | R |
| 13GV-18 | Vip3ArLr1 | 100 | 100 | 90.4 | 96.80 ± 5.54 | HR |
| 13GV-30 | Vip3ArLr1 | 90.4 | 90.4 | 90.4 | 90.40 ± 0.00 | HR |
| 13GV-38 | Vip3ArLr1 | 51.6 | 51.6 | 51.6 | 51.60 ± 0.00 | MR |
| TN-1 | Insect-susceptible control | 3.2 | −6.4 | 3.2 | 0 | S |

TABLE 7

Identification of resistance to artificially inoculated Chilo suppressalis for the stems of Vip3ArLr1 and control Vip3Aa1 transformed lines (2013).

| Transformed line | Gene | Corrected mortality % for each plant line | | | Average corrected mortality % | Resistance rating |
|---|---|---|---|---|---|---|
| | | 1 | 2 | 3 | | |
| Nipponbare | Parent control | 30.0 | 20.0 | 10.0 | 20.00 ± 10.00 | MR |
| 13GV-2 | Vip3Aa1 | 10.0 | −10.0 | 50.0 | 16.67 ± 30.55 | S |
| 13GV-12 | Vip3ArLr1 | 60.0 | 70.0 | 70.0 | 66.67 ± 5.77 | R |
| 13GV-18 | Vip3ArLr1 | 80.0 | 100 | 90.0 | 90.00 ± 10.00 | HR |
| 13GV-30 | Vip3ArLr1 | 40.0 | 100 | 100 | 80.00 ± 34.64 | R |
| 13GV-38 | Vip3ArLr1 | 30.0 | 70.0 | 10.0 | 36.67 ± 30.55 | MR |
| TN-1 | Insect-susceptible control | 0 | −10.0 | 10.0 | 0 | S |

TABLE 8

Identification of resistance to artificially inoculated
*Chilo suppressalis* for the plants of Vip3ArLr1
and control Vip3Aa1 transformed lines (2013).

| Transformed line | Gene | Dead heart rate on Day 15 (%) | Dead heart rate on Day 21 (%) |
|---|---|---|---|
| Nipponbare | Parent control | 25.00 | 50.00 |
| 13GV-2 | Vip3Aa1 | 10.00 | 75.00 |
| 13GV-12 | Vip3ArLr1 | 0.00 | 0.00 |
| 13GV-18 | Vip3ArLr1 | 0.00 | 0.00 |
| 13GV-30 | Vip3ArLr1 | 0.00 | 0.00 |
| 13GV-38 | Vip3ArLr1 | 0.00 | 5.00 |
| TN-1 | Insect-susceptible control | 100 | 100 |

Table 9 to 11 are the identification results of resistance to natural outbreak and artificial inoculation of *Cnaphalocrocis medinalis* Guenee for the 4 independent transformed lines and respective sister lines thereof. The rate of roll leaf of the natural outbreak and the average corrected mortality of artificial inoculation for the transformed line 12GV-43 and its respective sister line 13GV-38 are 12.5% and no greater than 20%, respectively, while the two indicators for all the other 3 independent transformed lines and respective sister lines thereof are less than 2%, and 100%, respectively, which are significantly different from the parent and insect-susceptible control lines. At this point, the new germplasm of Vip3ArLr1 transgenic insect-resistant rice was successfully created. The germplasm may be further used as parent to breed its derived lines using conventional backcross breeding process plus modern molecular marker-assisted selection, and to eventually breed superior and new transgenic insect-resistant lines.

TABLE 9

Identification of resistance to naturally occurring
*Cnaphalocrocis medinalis* Guenee for Vip3ArLr1
and control Vip3Aa1 transformed lines (2012).

| Transformed line | Gene | Rate of roll leaf (%) |
|---|---|---|
| 12GV-3 | Vip3Aa1 | 40.63 |
| 12GV-19 | Vip3ArLr1 | 0.00 |
| 12GV-26 | Vip3ArLr1 | 0.00 |
| 12GV-37 | Vip3ArLr1 | 0.00 |
| 12GV-43 | Vip3ArLr1 | 12.50 |

TABLE 10

Identification of resistance to naturally occurring
*Cnaphalocrocis medinalis* Guenee for Vip3ArLr1
and control Vip3Aa1 transformed lines (2013).

| Transformed line | Gene | Rate of roll leaf (%) |
|---|---|---|
| Nipponbare | Parent control | 43.33 |
| 13GV-1 | Vip3Aa1 | 30.00 |
| 13GV-12 | Vip3ArLr1 | 0.00 |
| 13GV-18 | Vip3ArLr1 | 0.00 |
| 13GV-30 | Vip3ArLr1 | 1.67 |
| 13GV-38 | Vip3ArLr1 | 18.33 |
| TN-1 | Insect-susceptible control | 100.00 |

TABLE 11

Identification of resistance to artificially inoculated *Cnaphalocrocis medinalis* Guenee
for the leaves of Vip3ArLr1 and control Vip3Aa1 transformed lines (2013).

| Transformed line | Gene | Corrected mortality % for each plant line | | | Average corrected mortality % | Resistance rating |
|---|---|---|---|---|---|---|
| | | 1 | 2 | 3 | | |
| Nipponbare | Parent control | 4.0 | 16.0 | 28.0 | 16.0 ± 12.00 | S |
| 13GV-2 | Vip3Aa1 | 16.0 | −20.0 | 4.0 | 0.0 ± 18.00 | S |
| 13GV-12 | Vip3ArLr1 | 100 | 100 | 100 | 100 ± 0.00 | HR |
| 13GV-18 | Vip3ArLr1 | 100 | 100 | 100 | 100 ± 0.00 | HR |
| 13GV-30 | Vip3ArLr1 | 100 | 100 | 100 | 100 ± 0.00 | HR |
| 13GV-38 | Vip3ArLr1 | 40.0 | 28.0 | −8.0 | 20.0 ± 24.98 | MR |
| TN-1 | Insect-susceptible control | 4.0 | −20.0 | 16.0 | 0 | S |

Finally, it should also be noted that those listed above are only some specific examples of this invention. In fact, this present invention is not only limited to the examples above, but may also vary to a great extent. As a result, all the variations that can be directly derived or suggested from the disclosure of the invention by one of ordinary skill in the art should be considered as within the scope of the invention.

REFERENCES (1) Tang, Wei, Yang, Zhou. Development of Transgenic Insect-resistant Indica Rice with a cry1Ab Gene. Journal of Huazhong Agricultural University, 2007, 26 (2): 159-160.
(2) Han, Lanzhi, Hou, Maolin, Peng, Yufa et al. Artificial feedstuff of striped rice borer, preparation method thereof and breeding method. Chinese Invention Patent. 200910080336.
(3) Li, Changyou, Li, Guoxun, Zhang, Jie, Song, Fuping & Huang, Dafang. Biological characteristics of *Bacillus thuringiensis* strain B-Hm-16 and identification of its cry-type genes. Journal of Qingdao Agricultural University (NATURAL SCIENCE), 2007, 24 (1): 1-5.
(4) Liu, Rongmei, Zhang, Jie, Gao, Jiguo et al. The research on vip3A Genes from *Bacillus thuriniensis* Strains. High Technology Letters. 2004, 14(9):39-42.

(5) Ni, Wanchao, Guo, Sandui. Development of Transgenic Insect-resistant Cotton Plants. Scientia Agricultura Sinica. 1998, 31(2):8-13.
(6) Zhu, Zhen, Deng, Zhaoyang, Wu, Qian & Xu, Honglin. Development of highly efficient insect-resistant transgenic rice. Journal of Yunnan University (NATURAL SCIENCE). 1999, 21.
(7) Barth H, Blocker D, Aktories K. The uptake machinery of clostridial actin ADP-ribosylating toxins-a cell delivery system for fusion proteins and polypeptide drugs. Naunyn Schmiedebergs Arch Pharmacol. 2002, 366(6):501-512.
(8) Barth H, Aktories K, Popoff M R, et al. Binary bacterial toxins: biochemistry, biology, and applications of common *Clostridium* and *Bacillus* proteins. Microbiol Mol Biol Rev. 2004, 68(3):373-402.
(9) Crickmore N. The Vip nomenclature. 2008.
(10) Estruch J, Warren G W, Mullins M A, et al. Vip3A, a novel *Bacillus thuringiensis* vegetative insecticidal protein with a wide spectrum of activities against lepidopteran insects. Proc Natl Acad Sci USA. 1996, 93(11): 5389-5394.
(11) Estruch J, Yu C G, Warren G W, et al. Plant pest control. WO/1998/044137, 1998.
(12) Estela A, Escriche B, Ferre J. Interaction of *Bacillus thuringiensis* toxins with larval midgut binding sites of *Helicoverpa armigera* (Lepidoptera:Noctuidae). Appl Environ Microbiol. 2004, 70(3):1378-1384.
(13) Fang J, Xu X, Wang P, Zhao J Z, Shelton A M, Cheng J, Feng M G, Shen Z. Characterization of Chimeric *Bacillus thuringiensis* Vip3 Toxins. Appl Environ Microbiol. 2007, 73(3): 956-961.
(14) Fraley R T, Rogers S G, Horsch R B, et al. Expression of bacterial genes in plant cells. Proc. NatL. Acad. Sci. USA. 1983, 80:4803-4807.
(15) Griffitts J S, Aroian R V. Many roads to resistance: how invertebrates adapt to Bt toxins. Bioessays. 2005, 27(6): 614-624.
(16) Gould F. Broad-spectrum resistance to *Bacillus thuringiensis* toxins in *Heliothis virescens*. Agriculture Sciences. 1992, 89:7986-7990.
(17) Han S, Craig J A, Putnam C D, Carozzi N B & Tainer J A. Evolution and mechanism from structures of an ADP-ribosylating toxin and NAD complex. Nature Structural & Molecular Biology. 1999, 6:932-936.
(18) Herdt R W. Research priorities for rice biotechnology. Rice biotechnology. 1991, 6,19-54.
(19) High S M, Cohen M B, Shu Q Y, et al. Achieving successful deployment of Bt rice. Trends Plant Sci. 2004, 9(6):286-292.
(20) Khush, G S. What it will take to feed 5.0 billion rice consumers in 2030. Plant Molecular Biology. 2005, 59:1-6.
(21) Lee M K. Resistance to *Bacillus thuringiensis* Cry1A δ-endotoxins in a laboratory-selected *Heliothis virescens* strain is related to receptor alteration. American Society for Microbiology. 1995, 61:3836-3842.
(22) Lee M K, Walters F S, Hart H, et al. The mode of action of the *Bacillus thuringiensis* vegetative insecticidal protein Vip3A differs from that of Cry1Ab delta-endotoxin. Appl Environ Microbiol. 2003, 69(8):4648-4657.
(23) Liu Q Q, Yao Q H, Wang H M, Gu M H. Endosperm-specific Expression of the Ferritin Gene in Transgenic Rice (*Oryza sativa* L.) Results in Increased Iron Content of Milling Rice. Journal of genetics and genomics. 2004, 31(5):518-524.
(24) McGaughey W H. Insect Resistance to the Biological Insecticide *Bacillus thuringiensis*. Science. 1985, 229 (4709):193-195.
(25) Perlak, F J. et al. Insect-resistance cotton plants. Bio/Technology. 1990, 8:939-943.
(26) Rang C, Gil P, Neisner N, Rice J V, Frutos R. Novel Vip3-related protein from *Bacillus thuringiensis*. Applied and Environmental Microbiology. 2005, 71(10):6276-6281.
(27) Yang R, Tang Q, Wang H, Zhang X, Pan G, Wang H, Tu J. Analyses of two rice (*Oryza sativa* L.) cyclin-dependent kinase inhibitors and effects of transgenic expression of OsiICK6 on plant growth and development. Annals of Botany. 2011, 107:1087-1101.
(28) Tabashnik B E, Liu Y B, Finson N, Masson L & Heckel D G. One gene in diamondback moth confers resistance to four *Bacillus thuringiensis* toxins. Proceedings of the National Academy of Sciences. 1997, 94:1640-1644.
(29) Tu J, Datta K, Alam M F, Khush G S, Datta S K. Expression and function of a hybrid Bt toxin gene in transgenic rice conferring resistance to pest. Plant Biotech. 1998, 15(4):195-203.
(30) Tu J, Zhang G, Datta K, Xu C, He Y, Zhang Q, Khush G S, and Datta S K. Field performance of transgenic elite commercial hybrid rice expressing *Bacillus thuringiensis* δ-endotoxin. Nature/Biotech. 2000, 18:1101-1104.
(31) Van Rie. Mechanism of insect resistance to the microbial insecticide *Bacillus thuringiensis*. Science. 1990, 247:72-74.
(32) Whalon M E, Wingerd B A. Bt mode of action and use. Arch Insect Biochem Physiol. 2003, 54:200-211.
(33) Warren G W, Koziel M G, Mullins M A. Auxiliary proteins for enhancing the insecticidal activity of pesticidal proteins. US patent. 1998, 5770696.
(34) Yu C G, Mullins M A, Warren G W, et al. The *Bacillus thuringiensis* vegetative insecticidal protein Vip3A lyses midgut epithelium cells of susceptible insects. Appl Environ Microbiol. 1997, 63(2):532-536.

The invention claimed is:

1. A modified nucleic acid molecule selected from the group consisting of:
   a) a nucleic acid molecule consisting of the nucleotide sequence of SEQ ID NO: 2 or the full-length complement thereof; and
   b) a nucleic acid molecule encoding a polypeptide consisting of the amino acid sequence of SEQ ID NO: 1.

2. A DNA construct comprising the modified nucleic acid molecule of claim 1.

3. The DNA construct of claim 2, further comprising a nucleic acid molecule encoding a heterologous polypeptide.

4. A host cell comprising the DNA construct of claim 2.

5. The host cell of claim 4, wherein the host cell is a bacterial cell or a eukaryotic cell.

6. The host cell of claim 5, wherein the host cell is a plant cell or a yeast cell.

7. The host cell of claim 6, wherein the host cell is a Gramineous plant cell.

8. The host cell of claim 7, wherein the host cell is a rice cell.

9. A host cell comprising the DNA construct of claim 3.

10. The host cell of claim 9, wherein the host cell is a bacterial cell or a eukaryotic cell.

11. The host cell of claim 10, wherein the host cell is a plant cell or a yeast cell.

12. The host cell of claim 11, wherein the host cell is a Gramineous plant cell.

13. The host cell of claim 12, wherein the host cell is a rice cell.

14. A modified polypeptide having insecticidal activity, wherein the modified polypeptide consists of the amino acid sequence of SEQ ID NO: 1.

15. A composition comprising the modified polypeptide of claim 14.

16. The composition of claim 15, wherein said composition is selected from the group consisting of powder, fines, pellet, granule, spray, emulsion, colloid and solution.

17. The composition of claim 15, comprising about 1 wt. %- about 99 wt. % of said polypeptide.

18. The composition of claim 16, comprising about 1 wt. %- about 99 wt. % of said polypeptide.

19. A method for controlling an insect pest population, comprising contacting said population with a pesticidally effective amount of the modified polypeptide of claim 14.

20. A method for killing an insect pest, comprising contacting or feeding said insect pest with a pesticidally effective amount of the modified polypeptide of claim 14.

21. A method for producing a modified polypeptide of having insecticidal activity, wherein the modified polypeptide consists of the amino acid sequence of SEQ ID NO: 1, comprising culturing the host cell of claim 9 under conditions for expressing a nucleic acid molecule encoding the modified polypeptide therein.

22. A plant having a DNA construct stably incorporated into its genome, said DNA construct comprising a modified nucleotide sequence encoding a protein having insecticidal activity, wherein said modified nucleotide sequence is selected from the group consisting of:
   a) a nucleic acid molecule consisting of the nucleotide sequence of SEQ ID NO: 2 or a full-length complement thereof; and
   b) a nucleic acid molecule encoding a polypeptide consisting of the amino acid sequence of SEQ ID NO: 1;
   wherein said nucleotide sequence is operably linked to a promoter, and wherein said promoter drives the expression of an encoding sequence in cells of the plant.

23. A method of protecting a plant against an insect pest, comprising introducing into said plant or cells thereof at least one expression vector comprising a modified nucleic acid molecule selected from the group consisting of:
   a) a nucleic acid molecule consisting of the nucleotide sequence of SEQ ID NO: 2; and
   b) a nucleic acid molecule encoding a polypeptide consisting of the amino acid sequence of SEQ ID NO: 1;
   wherein said modified nucleic acid molecule encodes an insecticidal polypeptide.

24. The method of claim 23, wherein said plant produces an insecticidal polypeptide having pesticidal activity against an insect pest.

25. A plant breeding method, comprising introducing into a plant or cells thereof at least one expression vector comprising a modified nucleic acid molecule selected from the group consisting of:
   a) a nucleic acid molecule consisting of the nucleotide sequence of SEQ ID NO: 2; and
   b) a nucleic acid molecule encoding a polypeptide consisting of the amino acid sequence of SEQ ID NO: 1;
   wherein said modified nucleic acid molecule encodes an insecticidal polypeptide.

26. The plant according to claim 22, wherein said plant is a Gramineous plant.

27. The plant according to claim 26, wherein said plant is rice.

28. The method according to claim 23, wherein said plant is a Gramineous plant.

29. The method according to claim 28, wherein said plant is rice.

30. The method according to claim 24, wherein said plant is a Gramineous plant.

31. The method according to claim 30, wherein said plant is rice.

32. The method according to claim 25, wherein said plant is a Gramineous plant.

33. The method according to claim 32, wherein said plant is rice.

34. The method according to claim 19, wherein said insect pest population is a lepidopteran pest population.

35. The method according to claim 34, wherein the lepidopteran pest population is rice borer or *Prodenia litura*.

36. The method according to claim 20, wherein said insect pest is a lepidopteran pest.

37. The method according to claim 36, wherein said lepidopteran pest is rice borer or *Prodenia litura*.

38. The method according to claim 21, wherein the modified polypeptide has insecticidal activity against a lepidopteran pest.

39. The method according to claim 38, wherein the lepidopteran pest is rice borer or *Prodenia litura*.

40. The plant according to claim 22, wherein the protein having insecticidal activity has insecticidal activity against a lepidopteran pest.

41. The plant according to claim 40, wherein the lepidopteran pest is selected from rice borer and *Prodenia litura*.

42. The method according to claim 23, wherein said insect pest is a lepidopteran pest.

43. The method according to claim 42, wherein the lepidopteran pest is rice borer or *Prodenia litura*.

44. The method according to claim 24, wherein said insect pest is a lepidopteran pest.

45. The method according to claim 44, wherein the lepidopteran pest is rice borer or *Prodenia litura*.

46. The method according to claim 25, wherein the insecticidal polypeptide has insecticidal activity against a lepidopteran pest.

47. The method according to claim 46, wherein the lepidopteran pest is rice borer or *Prodenia litura*.

* * * * *

UNITED STATES PATENT AND TRADEMARK OFFICE
CERTIFICATE OF CORRECTION

PATENT NO. : 9,879,056 B2  
APPLICATION NO. : 15/039234  
DATED : January 30, 2018  
INVENTOR(S) : Jumin Tu et al.

Page 1 of 1

It is certified that error appears in the above-identified patent and that said Letters Patent is hereby corrected as shown below:

On the Title Page

Item (71),
Under the subheading "APPLICANTS," Line 2: replace "Zheijiang Province" with --Zhejiang Province--

Signed and Sealed this
Thirty-first Day of July, 2018

Andrei Iancu
*Director of the United States Patent and Trademark Office*

UNITED STATES PATENT AND TRADEMARK OFFICE
CERTIFICATE OF CORRECTION

PATENT NO. : 9,879,056 B2
APPLICATION NO. : 15/039234
DATED : January 30, 2018
INVENTOR(S) : Jumin Tu et al.

It is certified that error appears in the above-identified patent and that said Letters Patent is hereby corrected as shown below:

On the Title Page

Item (73), under the subheading "ASSIGNEES," change the order of the assignees listed to "Zhejiang University, Hangzhou, Zhejiang (CN); China National Rice Research Institute, Hangzhou, Zhejiang (CN)."

Signed and Sealed this
Twenty-ninth Day of September, 2020

Andrei Iancu
*Director of the United States Patent and Trademark Office*

SEQUENCE LISTING

<160> NUMBER OF SEQ ID NOS: 4

<210> SEQ ID NO 1
<211> LENGTH: 789
<212> TYPE: PRT
<213> ORGANISM: Artificial Sequence
<220> FEATURE:
<223> OTHER INFORMATION: Description of Artificial Sequence: Modified Bacillus thuringiensis Vip3 protein

<400> SEQUENCE: 1

Met Asn Met Asn Asn Ala Lys Leu Asn Ala Arg Ala Leu Pro Ser Phe

-continued

```
1               5                   10                  15
Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Ser Asn Leu Thr Leu
            35                  40                  45

Asp Glu Ile Leu Lys Asn Gln Gln Leu Leu Asn Glu Ile Ser Gly Lys
            50                  55                  60

Leu Asp Gly Val Asn Gly Ser Leu Asn Asp Leu Ile Ala Gln Gly Asn
65                  70                  75                  80

Leu Asn Thr Glu Leu Ala Lys Gln Ile Leu Lys Val Ala Asn Glu Gln
                85                  90                  95

Asn Gln Val Leu Asn Asp Val Asn Asn Lys Leu Asp Ala Ile Asn Ser
                100                 105                 110

Met Leu Lys Ile Tyr Leu Pro Lys Ile Thr Ser Met Leu Ser Asp Val
                115                 120                 125

Met Lys Gln Asn Tyr Val Leu Ser Leu Gln Ile Glu Tyr Leu Ser Lys
            130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Met
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Pro Pro Ala Asp Ile Leu Asp Glu
            195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
            275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Ala Lys Gly Ser Asn Glu Asp Thr Lys Met Ile Val Glu Ala Lys
            340                 345                 350

Pro Gly Tyr Val Leu Val Gly Phe Glu Met Ser Asn Asp Ser Ile Thr
            355                 360                 365

Val Leu Lys Ala Tyr Gln Ala Lys Leu Lys Lys Asp Tyr Gln Ile Asp
            370                 375                 380

Lys Asp Ser Leu Ser Glu Ile Ile Tyr Ser Asp Thr Asp Lys Leu Leu
385                 390                 395                 400

Cys Pro Asp Gln Ser Glu Gln Ile Tyr Tyr Thr Lys Asn Ile Ala Phe
                405                 410                 415

Pro Asn Glu Tyr Val Ile Thr Lys Ile Ala Phe Thr Lys Lys Met Asn
            420                 425                 430
```

Ser Leu Arg Tyr Glu Ala Thr Ala Asn Phe Tyr Asp Ser Ser Thr Gly
        435                 440                 445

Asp Ile Asp Leu Asn Lys Thr Lys Val Glu Ser Ser Glu Ala Glu Tyr
450                 455                 460

Ser Met Leu Lys Ala Ser Asp Asp Glu Val Tyr Met Pro Leu Gly Leu
465                 470                 475                 480

Ile Ser Glu Thr Phe Leu Asn Pro Ile Asn Gly Phe Arg Leu Ala Val
                485                 490                 495

Asp Glu Asn Ser Arg Leu Val Thr Leu Thr Cys Arg Ser Tyr Leu Arg
                500                 505                 510

Glu Thr Leu Leu Ala Thr Asp Leu Asn Asn Lys Glu Thr Lys Leu Ile
            515                 520                 525

Val Pro Pro Asn Val Phe Ile Ser Asn Ile Val Glu Asn Gly Ser Ile
        530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
                580                 585                 590

Thr Glu Tyr Val Ile Gln Tyr Thr Val Lys Gly Lys Pro Ser Ile His
            595                 600                 605

Leu Lys Asp Glu Asn Thr Gly Tyr Ile His Tyr Glu Asp Thr Asn Asn
        610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
                660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
        690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
                740                 745                 750

Ser Glu Met Phe Thr Thr Lys Phe Glu Lys Asp Asn Phe Tyr Ile Glu
            755                 760                 765

Leu Ser Gln Gly Asn Asn Leu Tyr Gly Gly Pro Ile Val His Phe Tyr
770                 775                 780

Asp Val Ser Ile Lys
785

<210> SEQ ID NO 2
<211> LENGTH: 2374
<212> TYPE: DNA
<213> ORGANISM: Artificial Sequence
<220> FEATURE:
<223> OTHER INFORMATION: Description of Artificial Sequence: Nucleotide
      sequence encoding modified Bacillus thuringiensis Vip3 protein

```
<400> SEQUENCE: 2
aacaatgaac atgaacaacg ccaagctcaa cgcccgcgcc ctcccgtcct tcatcgacta      60
cttcaacggc atctacggct tcgccaccgg catcaaggac atcatgaaca tgatcttcaa     120
gacggacacc ggctccaacc tcaccctcga cgagatcctc aagaaccagc agctcctcaa     180
cgagatctcc ggcaagctcg acggcgtcaa cggcagcctc aacgacctca tcgcccaggg     240
caacctcaac accgagctcg ccaagcagat cctcaaggtc gccaacgagc agaaccaggt     300
cctcaacgac gtcaacaaca agctcgacgc gatcaactcg atgctcaaga tctacctccc     360
gaagatcacc tccatgctct ccgacgtcat gaagcagaac tacgtgctca gcctccagat     420
cgagtacctc tccaagcagc tccaggagat ctccgacaag ctcgacatca tcaacgtcaa     480
cgtgctcatc aactccacgc tcaccgagat caccccggcg taccagcgca tgaagtacgt     540
gaacgagaag ttcgaggagc tcaccttcgc caccgagacc accctcaagg tcaagaagga     600
cagcccgccg gccgacatcc tcgacgagct caccgagctc accgagctcg cgaagtccgt     660
caccaagaac gacgtggacg gcttcgagtt ctacctcaac accttccacg acgtcatggt     720
cggcaacaac ctcttcggcc gctccgccct caagaccgcc tcggagctca tcgccaagga     780
gaacgtgaag acctccggct ccgaggtcgg caacgtctac aacttcctca tcgtcctcac     840
cgccctccag gccaaggcct tcctcaccct caccacctgc cgcaagctcc tcggcctcgc     900
cgacatcgac tacacctcca tcatgaacga gcacctcaac aaggagaagg aggagttccg     960
cgtcaacatc ctccccaccc tctccaacac cttctccaac ccgaactacg ccaaggccaa    1020
gggctccaac gaggacacca agatgatcgt ggaggccaag ccgggctacg tcctcgtcgg    1080
cttcgagatg agcaacgact ccatcaccgt cctcaaggcc taccaggcca agctcaagaa    1140
ggactaccag atcgacaagg actcgctctc cgagatcatc tactccgaca cggacaagct    1200
cctctgcccg gaccagtccg agcagatcta ctacaccaag aacatcgcct tcccgaacga    1260
gtacgtcatc accaagatcg ccttcaccaa gaagatgaac tccctccgct acgaggcgac    1320
cgcgaacttc tacgactcct ccaccggcga catcgacctc aacaagacca aggtcgagtc    1380
ctccgaggcg gagtactcca tgctcaaggc ctccgacgac gaggtctaca tgccgctcgg    1440
cctcatctcc gagaccttcc tcaacccgat caacggcttc cgcctcgccg tcgacgagaa    1500
ctcccgcctc gtcaccctca cctgccgctc tacctccgc gagaccctcc tcgcgaccga    1560
cctcaacaac aaggagacca agctcatcgt cccgccgaac gtcttcatca gcaacatcgt    1620
cgagaacggc tccatcgagg aggacaacct cgagccgtgg aaggcgaaca acaagaacgc    1680
gtacgtcgac cacaccggcg gcgtgaacgg caccaaggcg ctctacgtcc acaaggacgg    1740
cggcatctcc cagttcatcg gcgacaagct caagccgaag accgagtacg tcatccagta    1800
caccgtcaag ggcaagccct ccatccacct caaggacgag aacaccggct acatcccacta    1860
cgaggacacc aacaacaacc tcgaggacta ccagaccatc aacaagcgct tcaccaccgg    1920
caccgacctc aagggcgtgt acctcatcct caagtcccag aacggcgacg aggcctgggg    1980
cgacaacttc atcatcctcg agatctcccc gtccgagaag ctcctctccc cggagctcat    2040
caacaccaac aactggacgt ccacgggctc caccaacatc agcggcaaca ccctcaccct    2100
ctaccagggc ggccgcggca tcctcaagca gaacctccag ctcgactcct tctccaccta    2160
ccgcgtgtac ttctccgtgt ccggcgacgc caacgtccgc atccgcaact cccgcgaggt    2220
gctcttcgag aagcgctaca tgagcggcgc caaggacgtc tccgagatgt tcaccaccaa    2280
gttcgagaag gacaacttct acatcgagct ctcccagggc aacaacctct acggcggccc    2340
```

```
                                                                    -continued gatcgtccac ttctacgacg tctccatcaa gtaa                                                2374

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
gctgttatgc ggccattgtc                                                                  20

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
gacgtctgtc gagaagtttc                                                                  20
```